USO10705018B2

United States Patent
Soyemi et al.

(10) Patent No.: US 10,705,018 B2
(45) Date of Patent: Jul. 7, 2020

(54) FLUORESCENCE BASED GLOBAL FUEL ANALYSIS METHOD

(71) Applicant: Authentix, Inc., Addison, TX (US)

(72) Inventors: Olusola Soyemi, Little Elm, TX (US); Anahita Kyani, Plano, TX (US)

(73) Assignee: Authentix, Inc., Addison, TX (US)

( * ) Notice: Subject to any disclaimer, the term of this patent is extended or adjusted under 35 U.S.C. 154(b) by 24 days.

(21) Appl. No.: 16/234,928

(22) Filed: Dec. 28, 2018

(65) Prior Publication Data

US 2019/0204290 A1    Jul. 4, 2019

Related U.S. Application Data

(60) Provisional application No. 62/611,330, filed on Dec. 28, 2017, provisional application No. 62/720,419, filed on Aug. 21, 2018.

(51) Int. Cl.
*G01N 21/64* (2006.01)
*G01N 33/28* (2006.01)
*C10L 1/00* (2006.01)

(52) U.S. Cl.
CPC .............. *G01N 21/64* (2013.01); *C10L 1/003* (2013.01); *G01N 33/2882* (2013.01)

(58) Field of Classification Search
None
See application file for complete search history.

(56) References Cited

U.S. PATENT DOCUMENTS

| 5,525,516 A | 6/1996 | Krutak et al. |
| 5,710,046 A | 1/1998 | Rutledge et al. |
| 5,723,338 A | 3/1998 | Rutledge et al. |
| 5,804,447 A | 9/1998 | Albert et al. |

(Continued)

FOREIGN PATENT DOCUMENTS

WO    2011037894 A1    3/2011

OTHER PUBLICATIONS

Filing Receipt and specification of a related priority U.S. Appl. No. 62/611,330, filed Dec. 28, 2017, 82 pages.

(Continued)

*Primary Examiner* — Violeta A Prieto
(74) *Attorney, Agent, or Firm* — Conley Rose, P.C.; Rodney B. Carroll

(57) ABSTRACT

A method of fuel analysis comprising subjecting a fuel sample comprising a fuel marker and a fuel matrix to fluorescence spectroscopy to generate a measured emission spectrum comprising a first spectral component (type and amount of marker in sample), a second spectral component (spectral perturbation), and a third spectral component (matrix fluorescence); deconvoluting the measured emission spectrum to yield a deconvoluted measured emission spectrum (first and second spectral components) via removal of third spectral component; decoupling the deconvoluted measured emission spectrum to yield a corrected emission spectrum (first spectral component) via a projection function which orthogonally projects the deconvoluted measured emission spectrum onto a subspace devoid of the second spectral component; and determining the amount of fuel marker in the fuel sample from the corrected emission spectrum. The method of fuel analysis comprises temperature corrections.

20 Claims, 13 Drawing Sheets

(56) References Cited

U.S. PATENT DOCUMENTS

| | | | |
|---|---|---|---|
| 5,843,783 A | 12/1998 | Rutledge et al. | |
| 5,928,954 A | 7/1999 | Rutledge et al. | |
| 7,157,611 B2 | 1/2007 | Banavali et al. | |
| 8,592,213 B2* | 11/2013 | Wilkinson | G01N 21/3577 |
| | | | 436/27 |
| 9,291,609 B2* | 3/2016 | Earl | G01N 33/22 |
| 9,995,681 B2* | 6/2018 | Conroy | G01N 21/643 |
| 10,351,789 B2* | 7/2019 | Conroy | G01N 21/643 |
| 2005/0019939 A1 | 1/2005 | Spall et al. | |
| 2008/0194446 A1 | 8/2008 | Elbert et al. | |
| 2009/0189086 A1 | 7/2009 | Gessner et al. | |
| 2010/0011656 A1 | 1/2010 | Gessner et al. | |
| 2011/0229983 A1* | 9/2011 | Wilkinson | G01N 33/2882 |
| | | | 436/501 |
| 2013/0179090 A1* | 7/2013 | Conroy | G01N 21/643 |
| | | | 702/25 |
| 2013/0283893 A1* | 10/2013 | Earl | G01N 33/22 |
| | | | 73/61.71 |
| 2015/0355091 A1* | 12/2015 | Conroy | G01N 21/643 |
| | | | 250/459.1 |
| 2018/0371342 A1 | 12/2018 | Conroy et al. | |

OTHER PUBLICATIONS

Filing Receipt and specification of a related priority U.S. Appl. No. 62/720,419, filed Aug. 21, 2018, 16 pages.

Fritsch, F. N., et al., "Monotone Piecewise Cubic Interpolation," SIAM Journal on Numerical Analysis, 1980, pp. 238-246, vol. 17, No. 2, Society for Industrial and Applied Mathematics.

Jaumot, Joaquim, et al., "A graphical user-friendly interface for MCR-ALS: a new tool for multivariate curve resolution in MATLAB," Chemometrics and Intelligent Laboratory Systems, 2005, pp. 101-110, vol. 76, No. 1.

Boulet, Jean-Claude, et al., "Pretreatments by means of orthogonal projections", Chemometrics and Intelligent Laboratory Systems, 2012, pp. 61-69, vol. 117, Elsevier B.V.

Bland, J. Martin, et al., "Statistical methods for assessing agreement between two methods of clinical measurement," The Lancet, 1986, pp. 307-310.

Fearn, Tom, "Comparing standard deviations," NIR News, 1996, pp. 5-6, vol. 7, No. 5.

Boor, Carl de, "A Practical Guide to Splines," 1978, Springer Verlag, New York.

* cited by examiner

FLUORESCENCE BASED GLOBAL FUEL ANALYSIS METHOD

CROSS-REFERENCE TO RELATED APPLICATIONS

This application claims priority to U.S. Provisional Application No. 62/611,330 filed on Dec. 28, 2017 by Olusola Soyemi and entitled "Fluorescence Based Global Fuel Analysis Method," and U.S. Provisional Application No. 62/720,419 filed on Aug. 21, 2018 by Olusola Soyemi, et al. and entitled "Temperature Compensation Methods for Fluorescence-based Fuel Analysis," each of which is incorporated by reference herein in its entirety.

TECHNICAL FIELD

The present disclosure relates to methods of analyzing fuel compositions, more specifically methods of analyzing marked fuel compositions via fluorescence spectroscopy.

BACKGROUND

Fuels represent a crucial energy supply and an important revenue source. Based on their provenience and quality (e.g., different grades or types of fuel), fuels can be differentially priced, such as taxed fuel and subsidized fuel or tax-free fuel; kerosene; diesel fuel; low-octane gasoline; high-octane gasoline; etc. Fuels can be differentially priced for a variety of reasons. In some countries, liquid fuel, such as diesel fuel, kerosene, and liquefied petroleum gas, is subsidized or sold below market rates to provide more widespread access to resources. Fuel can also be subsidized to protect certain industry sectors, such as public transportation.

Fuel adulteration is a clandestine and profit-oriented operation that is conducted for financial gain, which operation is detrimental to the rightful owner. Sometimes, fuels can be adulterated by mixing together fuels from different sources to obscure the origin of one or more of the fuels. Other times, adulterated fuels can be obtained by mixing higher priced fuel with lower priced fuel (e.g., lower grade fuel) or adulterants such as solvents. In some cases, subsidized fuel can be purchased and then re-sold, sometimes illegally, at a higher price. For example, subsidized fuel can be purchased and then mixed with other fuel to disguise the origin of the subsidized fuel.

Fuel markers can be added to fuels to establish ownership and/or origin of fuel. Fuel adulteration can be assessed by determining the presence and concentration of fuel markers in a fuel sample via a variety of analytical techniques, such as fluorescence spectroscopy, gas chromatography (GC), mass spectrometry (MS), etc. Fuel markers can interact with their immediate environment (e.g., matrix), such as fuel, solvent, etc., surrounding the marker, and the effect of the matrix can hinder the analysis of a fuel sample for determining whether a fuel is adulterated or not.

The variable nature of fuel products renders them a challenging medium for fluorescence-based analysis. Changes in fluorescence absorbance and emission bands result from fluctuations in the structure of the solvation shell around a fluorophore. Moreover, spectral shifts (both bathochromic and hypsochromic) in the absorption and emission bands are often induced by a change in solvent mixture or composition; these shifts commonly referred to as solvatochromic shifts, are experimental evidence of changes in the solvation energy. In other words, when a fluorophore is surrounded by solvent molecules, its ground state and excited state are more or less stabilized by fluorophore-solvent interactions, depending on the chemical nature of both the fluorophore and solvent molecules.

Generally, measurement sensitivity of fluorescent markers in fuels using fluorescence spectroscopy is blunted by poor measurement precision across samples due to the complex interaction of marker and fuel fluorescence across a wide spectrum of fuel matrices/formulations. Sample to sample variation in fluorescence measurement quality results in poor overall marker quantitation accuracy, which limits the extent to which fluorescence-based portable analyzers may be used in providing real-time actionable insights into fuel adulteration and/or diversion activities. Conventional analytical approaches to determine fuel adulteration and mitigate matrix effects have significant limitations that preclude their utility in fuel authentication.

Further, accurate estimation of fluorescent markers in fuels using fluorescence spectroscopy requires a thermally controlled measurement environment because of the influence of temperature on sample fluorescence emission. Generally, there are three critical components (e.g., an excitation source such as a laser-based excitation source, a sample, and a detector such as a light dispersion module) that exhibit sensitivity to temperature to varying degrees in fluorimetric measurements. Consequently, thermo-electric cooling (TEC) modules are a critical part of bench top spectrometers. The use of fluorescence-based fuel monitoring devices under field deployment conditions requires a degree of portability that precludes the use of thermally controlled units. The incorporation of hardware components that mitigate the effects temperature, such as thermo-electric cooling (TEC) modules for example, does not only add to the size, weight and cost of the spectrometer, but also significantly increases the power consumption of the instrument and the consequent need of a sufficiently powerful (and thus relatively short-lived) battery for field testing use. Thus, there is an ongoing need to develop and/or improve methods for detecting fuel markers.

BRIEF SUMMARY

Disclosed herein is a method of fuel analysis comprising (a) subjecting a fuel sample to fluorescence spectroscopy to generate a measured emission spectrum, wherein the fuel comprises a fuel marker and a fuel matrix, and wherein the measured emission spectrum comprises a first spectral component corresponding to type and amount of fuel marker in the fuel sample, a second spectral component corresponding to a spectral perturbation, and a third spectral component corresponding to fuel matrix fluorescence, (b) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component, (c) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of at least a portion of the second spectral component to yield the corrected emission spectrum, and (d)

determining the amount of fuel marker in the fuel sample from the corrected emission spectrum.

Further disclosed herein is a method of fuel analysis comprising (a) acquiring a fuel sample, (b) subjecting the fuel sample to fluorescence spectroscopy to generate a measured emission spectrum, wherein the fuel comprises a fuel marker and a fuel matrix, wherein the measured emission spectrum comprises a first spectral component corresponding to type and amount of fuel marker in the fuel sample, a second spectral component corresponding to a spectral perturbation, and a third spectral component corresponding to fuel matrix fluorescence, and wherein the spectral perturbation comprises fuel marker solvatochromism, (c) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component, (d) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum, (e) determining the amount of fuel marker in the fuel sample from the corrected emission spectrum, and (f) determining adulteration of the fuel by comparing the amount of fuel marker in the fuel sample to a target amount of fuel marker, wherein the target amount of fuel marker is a known amount of fuel marker used to mark the fuel by a fuel supplier.

Further disclosed herein is a method of fuel analysis comprising (a) obtaining a measured emission spectrum, via fluorescence spectroscopy, from a fuel sample by utilizing a fluorescence spectrometer, wherein the fluorescence spectrometer comprises a detector and a temperature-controlled excitation source, wherein the fuel sample and the detector are not temperature-controlled; wherein the fuel comprises a fuel marker and a fuel matrix, wherein the measured emission spectrum comprises a first spectral component corresponding to type and amount of fuel marker in the fuel sample, a second spectral component corresponding to a spectral perturbation, and a third spectral component corresponding to fuel matrix fluorescence, and wherein the spectral perturbation comprises a temperature perturbation and/or a fuel matrix perturbation, (b) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component, (c) decoupling the deconvoluted measured emission spectrum to yield a corrected emission spectrum via a fuel matrix projection function, wherein the corrected emission spectrum comprises the first spectral component, and wherein the fuel matrix projection function orthogonally projects the deconvoluted measured emission spectrum onto a subspace devoid of at least a portion of the second spectral component to yield the corrected emission spectrum, and (d) determining the amount of fuel marker in the fuel sample from the corrected emission spectrum.

Further disclosed herein is a method of fuel analysis comprising (a) acquiring a fuel sample, (b) obtaining a measured emission spectrum, via fluorescence spectroscopy, from a fuel sample by utilizing a portable fluorescence spectrometer, wherein the fluorescence spectrometer comprises a detector and a temperature-controlled excitation source, wherein the fuel sample and the detector are not temperature-controlled, wherein the fuel comprises a fuel marker and a fuel matrix, wherein the measured emission spectrum comprises a first spectral component corresponding to type and amount of fuel marker in the fuel sample, a second spectral component corresponding to a spectral perturbation, and a third spectral component corresponding to fuel matrix fluorescence, wherein the spectral perturbation comprises a temperature perturbation and a fuel matrix perturbation; wherein the fuel matrix perturbation comprises fuel marker solvatochromism, and wherein the temperature perturbation comprises wavelength shift and/or bandwidth changes, (c) correcting the measured emission spectrum for wavelength to yield a wavelength-corrected measured emission spectrum by matching peak wavelength with a reference fuel marker fluorescence emission wavelength, (d) deconvoluting the wavelength-corrected measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component, (e) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum, (f) determining an apparent amount of fuel marker in the fuel sample at the fuel sample temperature from the corrected emission spectrum, (g) applying a correction factor to the apparent amount of fuel marker in the fuel sample at the fuel sample temperature to yield a corrected amount of fuel marker in the fuel sample at a reference temperature, and (h) determining adulteration of the fuel by comparing the corrected amount of fuel marker in the fuel sample to a target amount of fuel marker, wherein the target amount of fuel marker is a known amount of fuel marker used to mark the fuel by a fuel supplier.

Further disclosed herein is a method of fuel analysis comprising (a) placing a fuel sample in a fluorescence spectrometer; wherein the fluorescence spectrometer comprises a temperature-controlled detector and a temperature-controlled excitation source, wherein the temperature-controlled detector and the temperature-controlled excitation source are characterized by a spectrometer temperature, wherein the fuel sample is not temperature-controlled, wherein the fuel sample is characterized by a sample temperature, and wherein the sample temperature is different from the spectrometer temperature, wherein the fuel comprises a fuel marker, wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively, (b) acquiring, via the fluorescence spectrometer, two or more measured emission spectra of the fuel sample during the first half of the equilibration time period, (c) deriving a signal intensity corresponding to the fuel marker from each measured emission spectrum, (d) generating a signal intensity variation over time curve and a sample temperature variation over time curve, wherein the signal intensity decreases with the sample temperature increasing over time or increases with the sample temperature decreasing over time; and wherein the signal intensity decrease or increase follows an exponential decay or growth curve over time, respectively, (e) estimating a signal intensity corresponding to the fuel marker at the end of the equilibration time period, and (f) determining the amount of fuel marker in the fuel sample from the estimated signal intensity corresponding to the fuel marker at the end of the equilibration time period.

Further disclosed herein is a method of fuel analysis comprising (a) acquiring a fuel sample, (b) placing the fuel sample in a portable fluorescence spectrometer, wherein the fluorescence spectrometer comprises a temperature-controlled detector and a temperature-controlled excitation source, wherein the temperature-controlled detector and the temperature-controlled excitation source are characterized by a spectrometer temperature, wherein the fuel sample is not temperature-controlled, wherein the fuel sample is characterized by a sample temperature, and wherein the sample temperature is different from the spectrometer temperature, wherein the fuel comprises a fuel marker and a fuel matrix, wherein the sample, when allowed to equilibrate to the spectrometer temperature, undergoes a sample temperature increase or decrease to the spectrometer temperature over an equilibration time period, wherein the sample temperature increase or decrease follows an exponential growth or decay curve over time, respectively, (c) acquiring, via the fluorescence spectrometer, three measured emission spectra of the fuel sample during the first half of the equilibration time period, (d) deriving a signal intensity corresponding to the fuel marker from each measured emission spectrum, (e) generating a signal intensity variation over time curve and a sample temperature variation over time curve, wherein the signal intensity decreases with the sample temperature increasing over time or increases with the sample temperature decreasing over time, and wherein the signal intensity decrease or increase follows an exponential decay or growth curve over time, respectively, (f) estimating a signal intensity corresponding to the fuel marker at the end of the equilibration time period, (g) determining the amount of fuel marker in the fuel sample from the estimated signal intensity corresponding to the fuel marker at the end of the equilibration time period, and (h) determining adulteration of the fuel by comparing the amount of fuel marker in the fuel sample to a target amount of fuel marker, wherein the target amount of fuel marker is a known amount of fuel marker used to mark the fuel by a fuel supplier.

Further disclosed herein is a method of spectra correction comprising (a) placing a sample in a spectrometer, wherein the spectrometer comprises a temperature-controlled detector and a temperature-controlled excitation source, wherein the temperature-controlled detector and the temperature-controlled excitation source are characterized by a spectrometer temperature, wherein the sample is not temperature-controlled, wherein the sample is characterized by a sample temperature, and wherein the sample temperature is different from the spectrometer temperature, wherein the sample comprises an analyte, wherein the sample, when allowed to equilibrate to the spectrometer temperature, undergoes a sample temperature increase or decrease to the spectrometer temperature over an equilibration time period, wherein the sample temperature increase or decrease follows an exponential growth or decay curve over time, respectively, (b) acquiring, via the spectrometer, two or more measured spectra of the sample during the first half of the equilibration time period, (c) deriving a signal intensity corresponding to the analyte from each measured spectrum, (d) generating a signal intensity variation over time curve and a sample temperature variation over time curve, wherein the signal intensity decreases with the sample temperature increasing over time or increases with the sample temperature decreasing over time, and wherein the signal intensity decrease or increase follows an exponential decay or growth curve over time, respectively, (e) estimating a signal intensity corresponding to the analyte at the end of the equilibration time period, and (f) determining the amount of analyte in the sample from the estimated signal intensity corresponding to the analyte at the end of the equilibration time period.

BRIEF DESCRIPTION OF THE DRAWINGS

For a more complete understanding of the present disclosure and advantages thereof, reference will now be made to the accompanying drawings/figures in which.

DETAILED DESCRIPTION

Figures 1A, 1B, 1C:
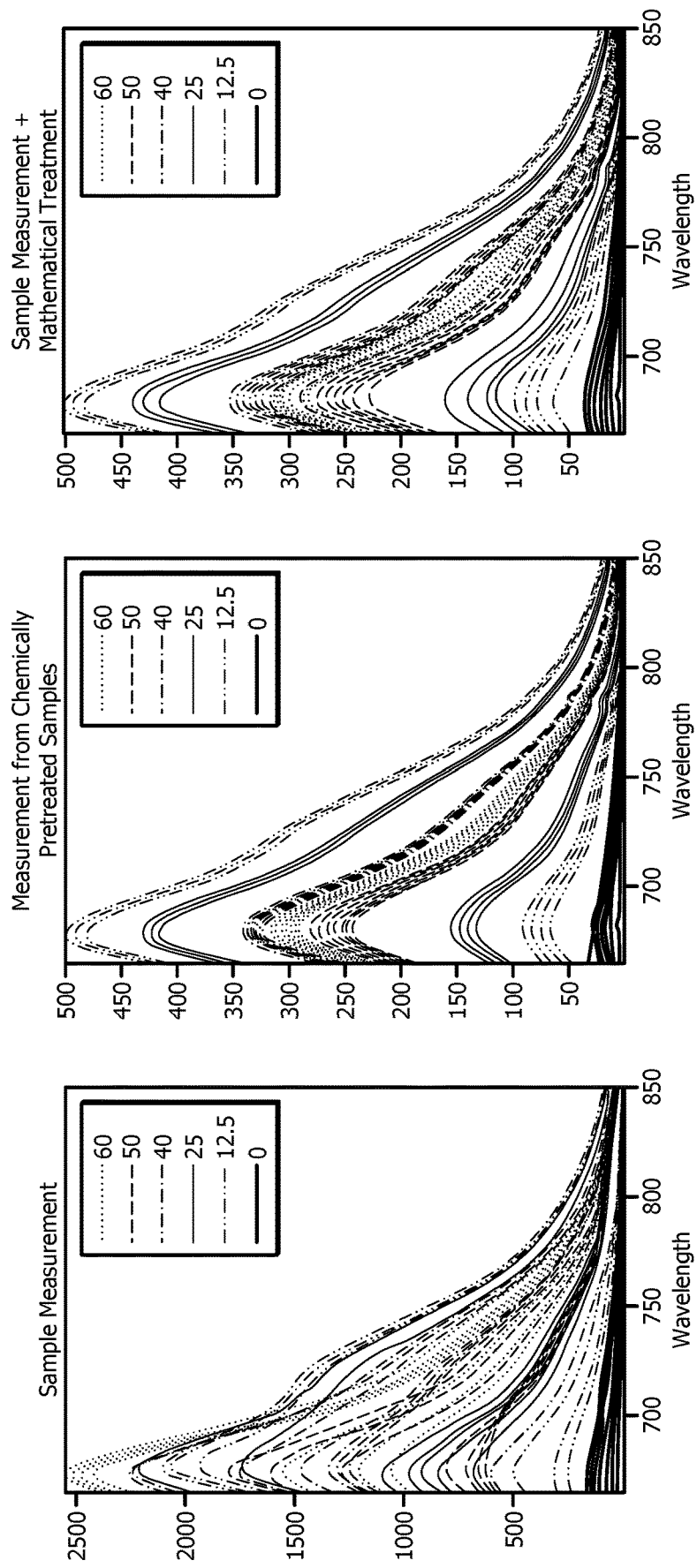
FIG. 1A displays fluorescence emission spectra measured for untreated samples.
FIG. 1B displays fluorescence emission spectra measured for chemically pre-treated samples.
FIG. 1C displays corrected emission spectra obtained from the spectra of FIG. 1A by orthogonal projection onto a subspace devoid of spectral perturbation.

Disclosed herein is a method of fuel analysis comprising (a) subjecting a fuel sample to fluorescence spectroscopy to generate a measured emission spectrum, wherein the fuel comprises a fuel marker and a fuel matrix, and wherein the measured emission spectrum comprises a first spectral component corresponding to type and amount of fuel marker in the fuel sample, a second spectral component corresponding to a spectral perturbation, and a third spectral component corresponding to fuel matrix fluorescence; (b) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; (c) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum; and (d) determining the amount of fuel marker in the fuel sample from the corrected emission spectrum. In an aspect, the method of fuel analysis can further comprise determining adulteration of the fuel by comparing the amount of fuel marker in the fuel sample to a target amount of fuel marker, wherein the target amount of fuel marker is a known amount of fuel marker used to mark the fuel by a fuel supplier. As used herein, "adulteration" of a fuel refers to altering, mixing, diluting, etc., of the fuel. In some cases, a fuel (e.g., a fuel taxed at a higher rate) can be combined (e.g., illegally) "as is" with another fuel (e.g., an untaxed fuel or fuel taxed at a lower rate) or solvent to form an adulterated (e.g., altered, mixed, diluted, etc.) fuel. For example, a fuel can be mixed with one or more other fuels, solvents, and the like, or combinations thereof. If undetected, the adulterated fuel can be sold, sometimes illegally, at the price of the fuel taxed at the higher rate to yield a profit. In some instances, the adulterated fuel can be potentially hazardous for the user, such as for example when a hazardous solvent is used for adulterating the fuel.

Further disclosed herein are methods for mitigating the effect of temperature on sample emission measurements from fuel analyzers, such as fluorescence spectrometers. The methods of fuel analysis as disclosed herein largely focus on mitigating the effect of temperature variations on the sample and/or the detector. Generally, the excitation sources can provide fluorescence excitation from a laser source or module, wherein the laser-based excitation sources are relatively easy to control for temperature. The methods of fuel analysis as disclosed herein can be applied to fluorescence spectrometers comprising laser-based excitation sources wherein (1) the detector is temperature-controlled, but sample is not temperature-controlled; or (2) neither the sample nor the detector are temperature-controlled. The methods for mitigating the effect of temperature on sample emission measurements from fuel analyzers as disclosed herein can significantly improve measurement accuracy and precision in temperature variable environments that would conventionally produce inaccurate and imprecise measurements. The methods for mitigating the effect of temperature on sample emission measurements from fuel analyzers as disclosed herein can compensate for the temperature-driven changes in spectral shape and intensity, leading to improvement in measurement accuracy and precision in temperature variable environments.

While the present disclosure will be discussed in detail in the context of a method of fuel analysis for determining adulteration of a fuel, it should be understood that such method or any steps thereof can be applied in a method of authenticating any other suitable liquid mixture. The liquid mixture can comprise any liquid mixture compatible with the disclosed methods and materials. As used herein, "authenticating" of a fuel or any other suitable liquid mixture refers to determining whether the fuel or any other suitable liquid mixture has been adulterated. Authenticating of a fuel or any other suitable liquid mixture can comprise detecting the presence and amount (e.g., concentration) of markers (e.g., fuel markers) in the fuel or any other suitable liquid mixture, as will be described in more detail later herein.

In an aspect, a method of fuel analysis can comprise a step of subjecting a fuel sample to fluorescence spectroscopy to generate a measured emission spectrum, wherein the fuel comprises a fuel marker and a fuel matrix, and wherein the measured emission spectrum comprises a first spectral component corresponding to type and amount of fuel marker in the fuel sample, a second spectral component corresponding to a spectral perturbation, and a third spectral component corresponding to fuel matrix fluorescence.

In an aspect, the fuel sample is a liquid sample.

In an aspect, the fuel sample can comprise a fuel. Generally, a fuel is a material or substance that stores potential energy that can be released as useful energy (e.g., heat or thermal energy, mechanical energy, kinetic energy, etc.) when the material undergoes a chemical reaction (e.g., combustion).

In an aspect, the fuel comprises a naturally-occurring material. Alternatively, the fuel comprises a synthetic material. Alternatively, the fuel comprises a mixture of a naturally-occurring and a synthetic material. Nonlimiting examples of fuels suitable for use in the present disclosure include gasoline, diesel, jet fuel, kerosene, liquefied petroleum gas, non-petroleum derived fuels, alcohol fuels, ethanol, methanol, propanol, butanol, biodiesel, maritime fuels, and the like, or combinations thereof. The fuel can further comprise one or more components typically found therein, e.g., oxygenates, antioxidants, antiknock agents, lead scavengers, corrosion inhibitors, viscosity modifiers, pour point depressants, friction modifiers, antiwear additives, dispersants, antioxidants, metal deactivators, and the like, or combinations thereof.

The fuel marker can be any suitable marking compound known to those of skill in the art to produce a signal in response to a stimulus. In some aspects, the fuel marker comprises a fluorescent marking compound. In an aspect, any suitable fluorescent fuel marker can be used for marking the fuels disclosed herein. Though specific fuel markers may be disclosed herein, any inorganic, organic, or metal complex structures that generate fluorescence emissions in a wavelength range of 500-1000 nm may be used, e.g., in a range of about 500 nm to about 900 nm, or alternatively from about 600 nm to about 800 nm.

Nonlimiting examples of fuel markers suitable for use in the present disclosure include phthalocyanines, naphthalocyanines, polymethine dyes, violanthrones, dibenzanthrones, isobenzanthrones, azadipyrromethenes, dipyrromethenes, rylenes, squaric acid dyes, rhodamines, oxazines, coumarins, cyanine fluorophores, and the like, or combinations thereof. Fluorescent fuel markers are described in more detail in U.S. Pat. Nos. 5,525,516; 5,804,447; 5,710,046; 5,723,338; 5,843,783; 5,928,954; and 7,157,611; U.S. Patent Publication Nos. 2005/0019939; 2008/0194446; 2009/0189086; and 2010/0011656; and PCT Patent Application No. WO 2011/037894; each of which is incorporated by reference herein in its entirety.

In an aspect, the fuel marker can be present within the marked fuel in an amount of from about 0.1 ppb to about 1,000 ppb, alternatively from about 0.5 ppb to about 500 ppb, or alternatively from about 1 ppb to about 200 ppb, based on the total weight of the marked fuel.

In an aspect, the method can comprise acquiring a fuel sample and subjecting a fuel sample to fluorescence spectroscopy for analysis, e.g., to determine the presence of the fuel marker in the fuel sample. Generally, fluorescence is a spectrochemical method of analysis where the molecules of an analyte (e.g., fuel marker) are excited by irradiation at a certain wavelength and emit radiation of a different wavelength, which can be recorded, for example, as an emission spectrum (e.g., measured emission spectrum). The emission spectrum provides information for both qualitative (e.g., presence or absence of fuel marker, fuel marker identity, type of fuel marker) and quantitative (e.g., amount of fuel marker) analysis. For example, when utilizing a technique (e.g., fluorescence spectroscopy) that involves a spectroscopic signal for a marking compound of interest (e.g., fuel marker), relevant parameters (e.g., extinction coefficient, absorption/emission maxima, etc.) may be used to determine the fuel sample concentration of the marking compound (e.g., fuel marker). Alternative suitable methodologies for determination of the amount of fuel marker present in a fuel sample may include the preparation of a calibration curve using standards of known concentration which can be subsequently utilized to calculate the amount of fuel marker in the sample of an unknown fuel marker concentration.

In some aspects, analysis of a fuel can be complicated by matrix effects. Generally, a "matrix" refers to an environment surrounding an analyte of interest (e.g., fuel marker), such as for example fuel components, solvent, laundering agents, masking agents, etc. In some cases, the matrix can influence the result of detecting a particular analyte, by interfering with the detection, and such interference can be referred for purposes of the disclosure herein as "matrix effect(s)." In some cases, matrix components can enhance the response of analytes (e.g., fuel markers) (matrix induced response enhancement); in other cases, matrix components can decrease analyte responses (matrix induced diminishment). For purposes of the disclosure herein, the term "matrix effects" encompasses the many different root causes of error that can occur in fluorescence based analyses as a result of matrix related issues. The matrix effects can be recorded as a spectral perturbation when measuring the emission spectrum of a fuel sample.

In an aspect, the spectral perturbation comprises fuel matrix effects that induce spectral inconsistencies in similarly marked fuel samples. In an aspect, the spectral perturbation comprises solvatochromism. Generally, solvatochromism refers to the ability of a chemical substance (e.g., fuel marker) to change color due to a change in solvent polarity, i.e., alter the fluorescence emission spectrum due to a change in solvent polarity (e.g., matrix effect). When a fluorescent molecule is moved from a gas phase into a solvent (e.g., liquid phase), a solvent-specific alteration of its optical properties results. Similar changes in optical properties of a fluorophore are also expected when the solvent used to solvate the fluorophore is changed; and these changes stem from each solvent possessing unique structural and electronic properties that interact differently with both the ground and excited states of the fluorophore. Such change of optical transition energies of the fluorescent molecule can be referred to as solvatochromism or solvatochromic shifting.

Without wishing to be limited by theory, the variable polarity of fuel matrices may induce marker-fuel interactions that cause intensity and/or wavelength shifts in the fluorescence emission spectra of some fluorescent fuel markers (i.e., solvatochromism). This poses a significant challenge to the development of accurate marker quantitation models. The method of fuel analysis as disclosed herein can mathematically remove the influence of such spectral perturbations from marked fuel emission spectra; and it applies to matrix effects (e.g., solvatochromism) that induce spectral inconsistencies in similarly marked fuel samples.

As will be appreciated by one of skill in the art, and with the help of this disclosure, the method of fuel analysis as disclosed herein does not work for fuel-marker interactions that either result in the removal of marker from the fuel or the quenching of marker fluorescence emission; including inner filter effects that stem from re-absorption of excitation and/or emission radiation from fuel matrices containing significant amounts of an absorbing dye, or quenching of fluorescence emission that may be facilitated by specific fuel additives.

Further, and as will be appreciated by one of skill in the art, and with the help of this disclosure, the implicit correction of the effect of solvatochromism in fuel fluorescence emission spectra with models that quantify marking levels is challenging because conventional models are often unable to separate the change in the spectral signature resulting from solvatochromism from the change in the analyte (e.g., fuel marker) concentration. A method of fuel analysis to explicitly correct for the effect of solvatochromism in spectra that stem from compromised (e.g., adulterated) fuel matrices is desired but difficult because the spectral signature of solvatochromism cannot be accurately determined across the possible range of fuel matrices that may be included in a quantitative model.

In an aspect, the method of fuel analysis as disclosed herein can provide for decoupling fluorescence emission spectra of fuel-marker mixtures by (i) removing additive baseline fluorescence contribution from a fuel-marker fluorescence emission spectrum via constrained deconvolution; and (ii) removing multiplicative fuel matrix signature from the baseline corrected spectrum using a mathematical implementation of fuel matrix regulation (e.g., "mathematical dilution"). The mathematical implementation of fuel matrix regulation mimics the mitigation of solvatochromism entailing the chemical pre-treatment of fuel-marker mixtures with an appropriate solvent, as will be described in more detail later herein.

In an aspect, the measured emission spectrum can comprise a first spectral component corresponding to type and amount of fuel marker in the fuel sample, a second spectral component corresponding to a spectral perturbation, and a third spectral component corresponding to fuel matrix fluorescence. In an aspect, the method of fuel analysis as disclosed herein can provide for the first spectral component, e.g., the spectral signature of the fuel maker by itself, without interferences from the matrix and/or fuel-matrix. The method of fuel analysis as disclosed herein removes the third spectral component via a background subtraction algorithm to yield a baseline corrected spectrum (e.g., deconvoluted measured emission spectrum); and removes the second spectral component via an orthogonal subspace projection algorithm to yield a corrected emission spectrum comprising the first spectral component (e.g., fuel marker component spectrum) without the second spectral component and the third spectral component.

In an aspect, the method of fuel analysis as disclosed herein can comprise a step of deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component (e.g., fuel marker signature) and the second spectral component (e.g., solvatochromism). For purposes of the disclosure herein, the third spectral component can also be referred to as "fuel fluorescence baseline" or "fuel fluorescence background." The result of the constrained deconvolution as disclosed herein is a spectrum (e.g., deconvoluted measured emission spectrum) in which the resulting signal is associated with the first spectral component (e.g., fuel marker signature) and the second spectral component (e.g., solvatochromism).

As will be appreciated by one of skill in the art, and with the help of this disclosure, a viable fuel background correction procedure must take into consideration the large variety of possible fuel background fluorescence emission spectrum signatures wherein the fuel-marker baseline is often not defined by a fixed shape or profile and cannot therefore be subjected simple linear or non-linear offsets. The method of fuel analysis comprising a step of deconvoluting the measured emission spectrum as disclosed herein can advantageously provide for achieving an accurate fuel baseline correction for fuel-marker fluorescence emission spectra wherein the pure marker component (e.g., fuel marker) is known but the fuel marker concentration is unknown. The method of fuel analysis comprising a step of deconvoluting the measured emission spectrum as disclosed herein deconvolutes the fluorescence emission baseline from the fuel marker contribution by using a reference solvent-marker emission spectrum in which the entirety of the emission contribution is from the marker, and not the solvent.

Figure 4:
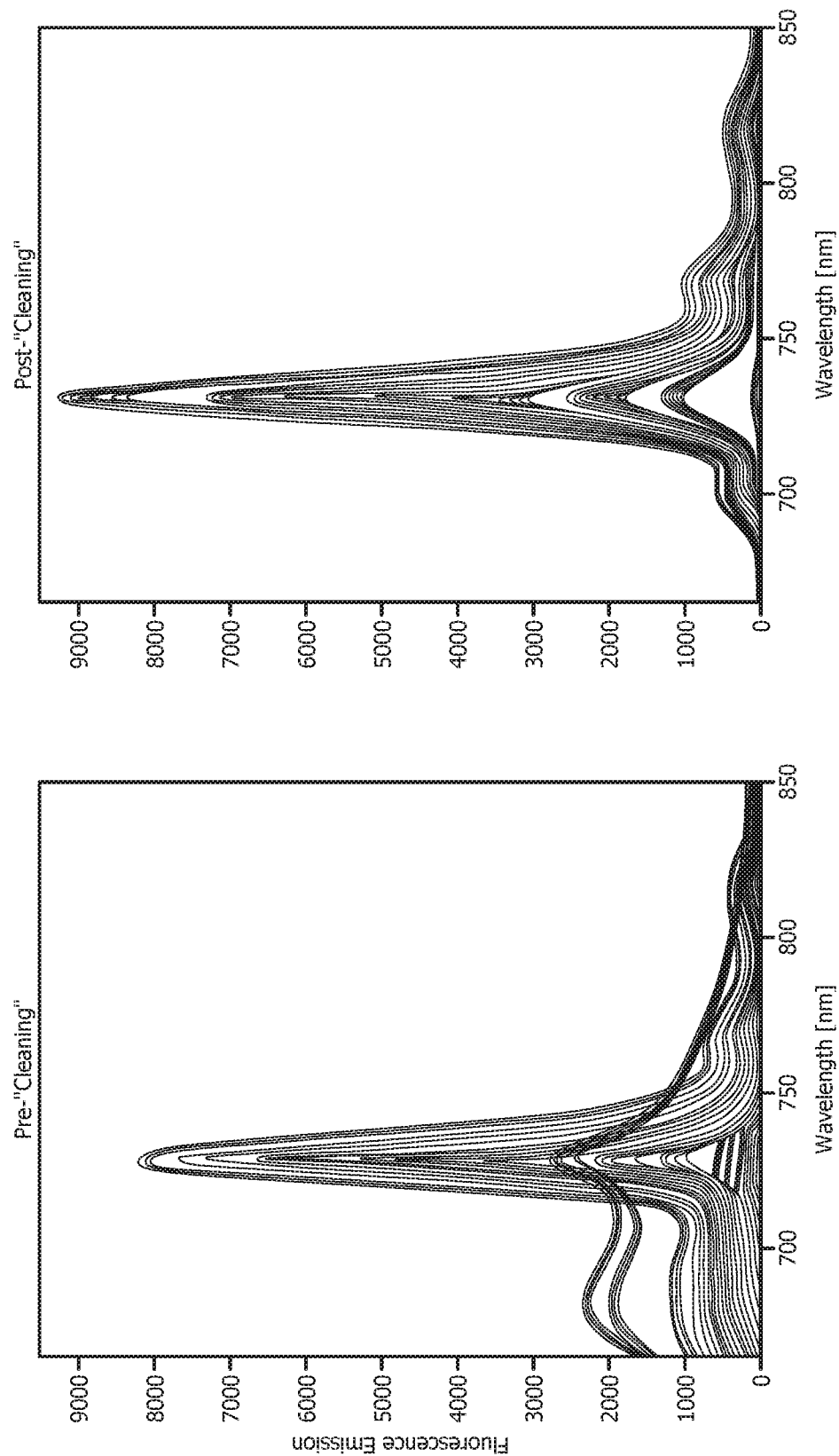
FIG. 4 displays data comparison of measured fluorescence emission spectra (left) and corrected emission spectra (right) generated via "mathematical dilution;"
Figure 6:
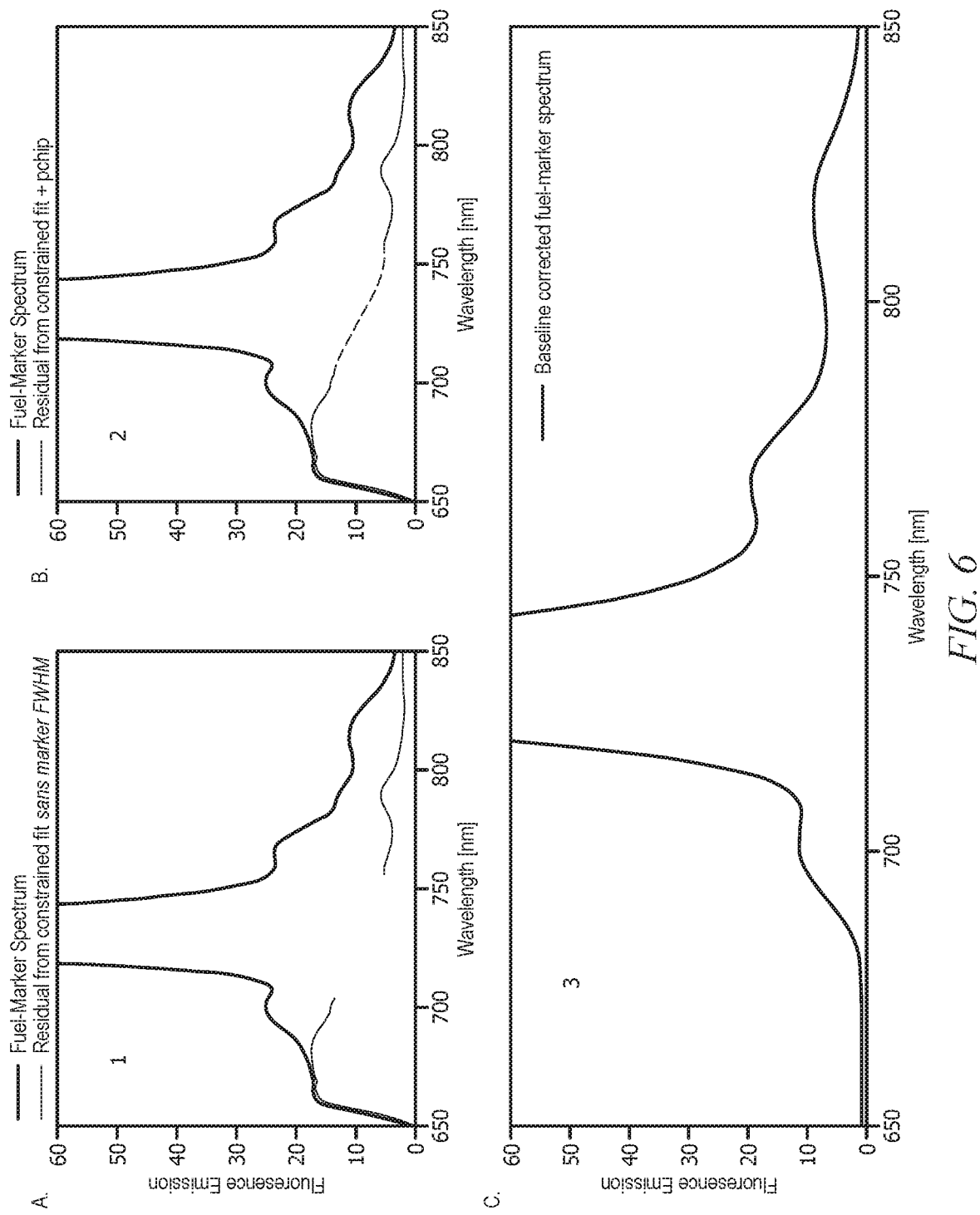
FIG. 6 displays plots depicting additive background correction via baseline deconvolution.

The method of fuel analysis comprising a step of deconvoluting the measured emission spectrum as disclosed herein is a 3 step process (e.g., deconvolution steps 1, 2, and 3), which is illustrated in FIGS. 4 and 6. FIG. 6 depicts the 3-step process for removing the additive contribution of the fuel background fluorescence, from the fuel-marker emission spectrum (e.g., measured emission spectrum). Removing additive baseline fluorescence contribution from a fuel-marker fluorescence emission spectrum via constrained deconvolution can be achieved as follows. Deconvolution step 1: First, an iterative fit of fuel-marker spectrum (e.g., measured emission spectrum) to a reference spectrum is performed to yield a residual spectrum. The iterative fit is centered around the full-width at half maximum (FWHM) of the fuel marker peak such that the portion of the residual spectrum (i.e., spectrum minus spectrum fit) that is outside the window described by the FWHM of the fuel marker encapsulates most of the fuel background from the original fuel-marker spectrum. Deconvolution step 1 is depicted in FIG. 6A. Deconvolution step 2: Next, the segment of the residual spectrum from the deconvolution step 1 corresponding to the FWHM of the marker emission spectrum is "filled in" using a shape-preserving piecewise cubic hermite interpolating polynomial (pchip) to yield a reconstituted residual spectrum, as illustrated in FIG. 6B by the dashed line. Shape-preserving pchip is described in more detail in A Practical Guide to Splines by C. de Boor, Springer-Verlag, New York, 1978.; and F. N. Fritsch and R. E. Carlson, Monotone Piecewise Cubic Interpolation, SIAM Journal on Numerical Analysis, 17 (1980), pp. 238-246; each of which is incorporated by reference herein in its entirety. The reconstituted residual spectrum corresponding to the third spectral component is equivalent to the fuel fluorescence baseline. Deconvolution step 3: Finally, the reconstituted residual spectrum is subtracted from the fuel-marker spectrum (e.g., measured emission spectrum) to yield the background corrected spectrum (e.g., deconvoluted measured emission spectrum).

Without wishing to be limited by theory, in contrast to multivariate curve resolution—alternating least squares (MCR-ALS) method, a spectrum deconvolution method that is able to estimate the pure component and concentration profiles from spectrum measurements, such as the method of fuel analysis comprising a step of deconvoluting the measured emission spectrum as disclosed herein, is advantageously more computationally efficient because it does not require as many tuning parameters as MCR-ALS in order to produce the desired baseline correction across a variety of fuel baseline types and/or shapes. MCR-ALS is described in more detail in J. Jaumot et al., A graphical user-friendly user interface for MCR-ALS: a new tool for multivariate curve resolution in MATLAB. Chemometrics and Intelligent Laboratory Systems; 76(1), 2005, 101-110; which is incorporated by reference herein in its entirety.

As will be appreciated by one of skill in the art, and with the help of this disclosure, the successful implementation of MCR-ALS requires several constraints (e.g., non-negativity, unimodality and closure) that improve the interpretability of estimated pure component spectra (including the marker emission spectrum and the baseline contribution from one or more components), as well as additional mathematical constraints for the ALS fit—e.g., local rank, window size, etc. Further, and without wishing to be limited by theory, the only tuning parameter required for the method of fuel analysis comprising a step of deconvoluting the measured emission spectrum as disclosed herein is the window size (win) that is used to extend the marker FWHM. The optimum value of FWHM±win can advantageously yield a better estimate of the interpolated baseline in deconvolution step 2, and can consequently yield an accurate baseline corrected spectrum (e.g., deconvoluted measured emission spectrum).

In an aspect, the method of fuel analysis comprising a step of deconvoluting the measured emission spectrum as disclosed herein is advantageously faster than the MCR-ALS method. As will be appreciated by one of skill in the art, and with the help of this disclosure, and without wishing to be limited by theory, the MCR-ALS method attempts the estimation of one or more components that may constitute the fluorescence background (depending on the fuel matrix) in addition to the fuel marker component; whereas the method of fuel analysis comprising a step of deconvoluting the measured emission spectrum as disclosed herein assumes a two-component model, i.e., the bulk background fluorescence (e.g., fuel fluorescence background) and the fuel marker fluorescence. Further, as will be appreciated by one of skill in the art, and with the help of this disclosure, and without wishing to be limited by theory, unlike in ALS, the iterative fit in deconvolution step 1 as disclosed herein can be accurately implemented with a 2-dimensional lookup table (e.g., fluorescence emission versus wavelength). The look-up table for deconvolution step 1 comprising of simulated marker-solvent spectra across a defined concentration range and a defined concentration value per spectrum, can be advantageously generated in real-time by scaling the reference spectrum which is defined by a known concentration of the fuel marker.

In an aspect, the method of fuel analysis comprising a step of deconvoluting the measured emission spectrum as disclosed herein can provide for computational flexibility that stems from the fact that the deconvolution does not require a priori knowledge of how many components constitute the fuel fluorescence baseline.

In an aspect, the method of fuel analysis as disclosed herein can comprise a step of decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum. In an aspect, decoupling the deconvoluted measured emission spectrum comprises the removal of multiplicative fuel matrix perturbation via the projection function. Decoupling the deconvoluted measured emission spectrum removes the second spectral component leaving the fluorescence signal associated with the fluorescent fuel marker (e.g., first spectral component), which can also be referred to as the pure marker spectral component or the pure marker spectrum.

Some conventional methods can correct for spectral perturbations stemming from chemical or physical phenomena even when the spectral signatures of these phenomena are unknown, for example as described in more detail in "Pretreatments by means of orthogonal projections" by Jean-Claude Boulet and Jean-Michel Roger, Chemometrics and Intelligent Laboratory Systems, volume 117, pp 61-69, 2012; which is incorporated by reference herein in its entirety. These conventional methods rely on experiments that capture the chemical signature of the targeted perturbation, but not the spectral perturbation of interest. A matrix of eigenvectors (P) that define a spectral subspace containing the spectral perturbations can be generated via matrix decomposition using singular value decomposition (SVD) or principal components analysis (PCA). The projection of a sample spectrum (containing contributions from the analyte as well as the spectral perturbation) onto a subspace that is orthogonal to P can effectively produce a corrected spectrum that is free of the spectral perturbation. Error removal via orthogonal projection can be conventionally implemented according to equation (1):

$$\hat{x} = x(I - PP_T) \quad (1)$$

wherein x is the measured spectrum (1×n wavelengths), $\hat{x}$ is the corrected spectrum (1×n wavelengths), P is the matrix describing the perturbation subspace (n wavelengths×a orthogonal columns that define the dimensions of the subspace), I is the (n×n) identity matrix, and superscript T denotes matrix transposition (i.e., matrix $P^T$ is the transpose of matrix P). However, and without wishing to be limited by theory, a subspace P that defines marker solvatochromism and is concurrently orthogonal to marker fluorescence emission cannot be defined by experimental design, and as such equation (1) cannot be applied to the measured emission spectrum and/or the deconvoluted measured emission spectrum to remove the spectral perturbation and yield the pure marker spectrum.

In some aspects, the fuel samples can be chemically pre-treated (e.g., chemically treated) to chemically mitigate the effect of solvatochromism on fuel marker fluorescence. In such aspects, fuel matrices containing the marker can be pre-treated with an appropriate solvent in a manner that equalizes the polarity across all the fuel matrices, effectively dampening the variation stemming from these polarity differences (e.g., effectively dampening solvatochromism).

In an aspect, a method of chemically pre-treating a fuel sample can comprise obtaining a first fuel sample comprising (a) a fuel and (b) a fuel marker; obtaining a homogeneity inducing material (also referred to herein as a "solvent"); contacting the homogeneity inducing material with an aliquot of the first fuel sample in a desired volumetric ratio of the homogeneity inducing material to the first fuel sample (e.g., a volumetric ratio of greater than or equal to about 7:1) to produce a second fuel sample; and determining an amount of the fuel marker in the second fuel sample using fluorescence spectroscopy.

The first fuel sample can comprise a fuel, a fuel marker, and a homogeneity-varying material. The homogeneity-varying material can also be referred to herein as a "signal-dampening material." As will be appreciated by one of skill in the art, and with the help of this disclosure, the fuel matrix comprises the fuel and the homogeneity-varying material. In some aspects, the homogeneity-varying material comprises one or more other refined fuel products, biofuels, fuel additives, oxygenates, common fuel adulterants, or combinations thereof. The homogeneity-varying material in the fuel may result from naturally occurring variances in the fuel, and/or from adulteration of the fuel with components prior to the addition of the markers. In some aspects, the signal-dampening material or homogeneity varying material is present in the fuel in an amount of from about 1 ppm to about 10 wt. %, alternatively from about 5 ppm to about 5 wt. %, or alternatively from about 10 ppm to about 1 wt. %. In an aspect, the signal-dampening material or homogeneity varying material reduces a signal intensity (e.g., a fluorescence signal intensity) of a marking compound (e.g., of a fluorescent marking compound) by an amount in the range of from about 1% to about 100%, alternatively from about 1% to about 95%, or alternatively from about 1% to about 90%.

Via addition of the homogeneity inducing material, the homogeneity of the fuel sample is increased. For example, in some aspects, a first or 'non-matrix-regulated' fuel sample has a first degree of homogeneity in the range of from about 0.1 to about 0.4, from about 0.1 to about 0.3, or from about 0.1 to about 0.2. The term "degree of homogeneity" as used herein refers to a scale of 0 to 1 wherein a pure sample comprising a solvated known compound is designated to have a degree of homogeneity of 1 while a sample comprising a plurality of compounds (e.g., greater than about 5) wherein at least one of the compounds is unknown is designated as having a degree of homogeneity of 0. In an aspect, the first fuel sample has a first homogeneity that is less than or equal to about 0.5, 0.4, 0.3, 0.2, or 0.1. In an aspect, the second or "matrix-regulated" fuel sample has a second degree of homogeneity in the range of from about 0.5 to about 1.0, alternatively from about 0.7 to about 0.95, or alternatively from about 0.8 to about 0.95. In some aspects, the second fuel sample has a second degree of homogeneity that is greater than or equal to about 0.5, 0.6, 0.7, 0.8, 0.9, or 0.95.

Without wishing to be limited by theory, the addition of the homogeneity inducing material may mitigate changes in fluorescence due to solvent effects by normalizing the solvent environment around the fluorophore by addition of consistent solvent to the sample. This approach may help minimize solvatochromic shifting in the fluorescence spectrum by ensuring that the fluorophore is always surrounded by the solvent molecules in solution, and hence can provide for a consistent fluorescence spectrum. Such approach can significantly improve quantitation results when fluorophores are present in varying solvents, providing the dilution is not so large as to approach the detection limits of the instrument being utilized to make the measurement.

In an aspect, the homogeneity inducing material comprises, consists, or consists essentially of one or more aliphatic hydrocarbons, aromatic hydrocarbons, petroleum distillates, halogenated aliphatic hydrocarbons, halogenated aromatic hydrocarbons, or combinations thereof. In some aspects, the homogeneity inducing material comprises, consists, or consists essentially of mesitylene (1,3,5-trimethylbenzene or TMB). In an aspect, the homogeneity inducing material is added to provide a desired volumetric ratio of the homogeneity inducing material to the first sample (e.g., aliquot comprising the fuel). For example, the desired volumetric ratio may be greater than or equal to about 2:1, 3:1, 4:1, 5:1, 6:1, 7:1, 8:1, 9:1, or 10:1. The homogeneity inducing material can be added such that the ratio of the homogeneity inducing material to the first fuel sample (e.g., an aliquot comprising the fuel) is in the range of from about 1:1 to about 15:1, from about 5:1 to about 10:1, or from about 7:1 to about 8:1. The homogeneity inducing material addition may provide a balance mitigating the solvent effect (where higher ratios may be better) and the loss of signal for detectability (where lower ratios may be better).

As will be appreciated by one of skill in the art, and with the help of this disclosure, while the fuel samples can be chemically pre-treated with a homogeneity inducing material to chemically mitigate the effect of solvatochromism on fuel marker fluorescence, the chemical pre-treatment method requires additional experimental steps and materials (e.g., homogeneity inducing material). The chemical pre-treatment of fuel samples to mitigate solvatochromism is described in more detail in U.S. patent application Ser. No. 15/632,532 filed Jun. 26, 2017 and entitled "A method of improving the accuracy when quantifying fluorescence markers in fuels," which is incorporated by reference herein in its entirety.

The method of chemically pre-treating fuel samples to mitigate the effect of solvatochromism on fuel marker fluorescence provides an avenue for an unconventional implementation of the orthogonal correction method in equation (1), wherein the desired outcome ($\hat{X}$) is defined by experimentation, and wherein the projection matrix ($PP^T$) is unknown. Equation (1) can be rearranged according to equation (2):

$$PP^T = X^{-1}(XI - \hat{X}) \tag{2}$$

wherein $X^{-1}$ is the Moore-Penrose inverse of spectral matrix X (m samples×n wavelengths) and $\hat{X}$ is the m×n matrix of spectra derived from chemically pre-treated fuel samples. Equation (2) can be used for estimating the n×n projection matrix ($PP^T$) from experimental data (e.g., fluorescence spectra) acquired for chemically pre-treated fuel samples, for a specific fuel marker. The estimated n×n projection matrix $PP^T$ can be plugged into equation (1), and equation (1) can provide for mathematically removing of solvatochromism from a measured emission spectrum of a fuel sample that has not been subjected to chemical pre-treatment, wherein the fuel sample has been marked with the same fuel marker that was used in the chemically pre-treated fuel samples that provided the data for estimating $PP^T$ via equation (2). The use of equations (1) and (2) to mitigate the effect of solvatochromism on fuel marker fluorescence involves the use of a quantitative model that correlates fuel marker concentration to fuel-marker fluorescence emission spectra using fluorescence spectral measurements that are generated from chemically pre-treated samples.

As will be appreciated by one of skill in the art, and with the help of this disclosure, and without wishing to be limited by theory, equation (2) estimates a subspace defined by the spectral perturbation (e.g., solvatochromism) via the projection matrix ($PP^T$). The subspace defined by the spectral perturbation allows for correcting the measured spectrum ($x_{measured}$) to yield a corrected spectrum ($x_{corrected}$) by using an equation of the following type: $x_{corrected} = x_{measured} - x_{measured} *$ projection_matrix (i.e., equation (1)).

In an alternative aspect, the method of fuel analysis as disclosed herein can comprise estimating a subspace devoid of the spectral perturbation, for example via the projection function. In an aspect, the projection function (W) orthogonally projects the fuel marker signal or spectral signal outside the fuel matrix space (e.g., onto a subspace that is devoid of the solvatochromism spectral perturbation), thereby producing a corrected emission spectrum that is independent of the fuel matrix. The method of fuel analysis as disclosed herein can provide for "mathematical dilution" of the measured emission spectra (e.g., deconvoluted measured emission spectra) to an extent where the corrected emission spectrum is not affected by the fuel matrix effect (e.g., solvatochromism effect) on the fuel marker fluorescence signal (e.g., corrected or pure marker emission spectra). The projection function (W) that estimates a subspace devoid of the spectral perturbation can allow for correcting the measured spectrum ($x_{measured}$) to yield a corrected spectrum ($x_{corrected}$) by using an equation of the following type: $x_{corrected} = x_{measured} *$ projection_matrix.

In some aspects, the projection function (W) can be derived by comparing an emission fluorescence spectrum of a marked fuel sample comprising a spectral perturbation with an emission fluorescence spectrum of the same marked fuel sample that has been chemically pre-treated to remove at least a portion of the spectral perturbation. The marked fuel sample that yields the emission fluorescence spectrum comprising a spectral perturbation and the marked fuel sample that is being chemically pre-treated to remove at least a portion of the spectral perturbation are substantially the same (i.e., prior to chemical pre-treatment). PCA or SVD can be used to generate factor scores and loadings matrices (e.g., via decomposition) from original fuel sample fluorescence emission spectrum measurements ($X_1$), as well as fluorescence emission spectrum measurements of chemically pre-treated samples ($X_2$). As will be appreciated by one of skill in the art, and with the help of this disclosure, $X_1$ and $X_2$ are derived from substantially similar samples subjected to no chemical pre-treatment and subjected to chemical pre-treatment, respectively. In an aspect, the subspace devoid of the second spectral component (e.g., spectral perturbation, solvatochromism) is based on the emission fluorescence spectrum of the chemically pre-treated marked fuel sample ($X_2$). The subspace devoid of the second spectral component is derived from the emission fluorescence spectrum of the chemically pre-treated marked fuel sample ($X_2$) via matrix decomposition analysis using SVD or PCA.

The projection function (W) can be defined according to equation (3):

$$W = P_1(T_1^T T_1)^{-1} T_1^T T_2 P_2^T \quad (3)$$

wherein $P_1/T_1$ and $P_2/T_2$ are the scores and loading matrices from the decomposition of $X_1$ and $X_2$, respectively. Matrix $T_1^T$ is the transpose of matrix $T_1$. Matrix $P_2^T$ is the transpose of matrix $P_2$. The rows for $P_1/P_2$ and $T_1/T_2$ are n (number of wavelengths) and m (number of samples), respectively. The columns for $P^1/T_1$ and $P_2/T_2$ are the number of reduced dimensions (a and b) that describe all the spectral variation in $X_1$ and $X_2$, respectively; wherein a and b are the optimum number of latent variables or the optimum number of factor space dimensions from the singular value decomposition of $X_1$ and $X_2$, respectively. $P_1(T_1^T T_1)^{-1} T_1^T$ is a portion of W that is used to project the perturbed spectra onto the subspace defined by $X_2$, wherein $X_2 = T_2 P_2^T$.

In an aspect, comparing an emission fluorescence spectrum of a marked fuel sample with an emission fluorescence spectrum of the chemically pre-treated marked fuel sample comprises determining a least square estimator (β) of a multiple linear regression (MLR) model that fits the emission fluorescence spectrum of the marked fuel sample to the emission fluorescence spectrum of the chemically pre-treated marked fuel sample. The term $(T_1^T T_1)^{-1} T_1^T T_2$ in equation (3) is the least squares estimator (β) of the MLR model that fits $T_1$ to $T_2$, which, and without wishing to be limited by theory, is essentially principal components regression (PCR), which is a regression analysis technique based on PCA. Equation (3) can thus be simplified in the form of equation (4) as follows:

$$W = P_1 \beta P_2^T \quad (4)$$

wherein the dimension of the MLR regression parameter β is a×b. Without wishing to be limited by theory, optimizing a and b can allow for tuning the projection function (W), which is an advantageous feature over the orthogonal correction approach described by equations (1) and (2). The projection function (W) is fuel marker specific; however, W advantageously affords the opportunity of being used for a variety of fuel matrices without having to record fluorescence emission spectra of chemically pre-treated samples when the fuel matrix changes.

In an aspect, the projection function (W) orthogonally projects the measured emission spectrum (x) onto a subspace devoid of the second spectral component (e.g., defined by $X_2$) to yield the corrected emission spectrum ($\hat{x}$) according to equation (5):

$$\hat{x} = xW \quad (5)$$

In other aspects, the projection function (W) can be derived by comparing an emission fluorescence spectrum of a marked fuel sample comprising a known amount of fuel marker and fuel with an emission fluorescence spectrum of one or more marked solvent solutions comprising a known amount of fuel marker and a solvent. The projection function (W) can be generated by comparing spectra that are derived from fuels that are marked with a known amount of fuel marker (e.g., matrix compromised fuel-marker mixtures) to spectra that are derived from solvent—marker mixtures that have known amounts or concentrations of fuel markers. Nonlimiting examples of solvents suitable for forming the marked solvent solutions as disclosed herein include aliphatic hydrocarbons, aromatic hydrocarbons, mesitylene (1,3,5-trimethylbenzene or TMB), petroleum distillates, halogenated aliphatic hydrocarbons, halogenated aromatic hydrocarbons, or combinations thereof. The fuel marker can be present in the marked solvent solutions in an amount of from about 0.1 ppb to about 1,000 ppb, alternatively from about 0.5 ppb to about 500 ppb, or alternatively from about 1 ppb to about 200 ppb, based on the total weight of the marked solvent solutions.

In an aspect, comparing an emission fluorescence spectrum of a marked fuel sample with an emission fluorescence spectrum of one or more marked solvent solutions further comprises PCR to yield the projection function (W), as previously described herein. In such aspect, each spectrum of a dataset comprising marked fuel spectra (e.g., deconvoluted measured emission spectra) is matched to a marked solvent spectrum of the same marker concentration. In such aspect, W can be derived by comparing known marked fuel samples with known marked solvent solutions, which contrasts the previously described method of deriving W by comparing of each marked fuel spectrum (e.g., deconvoluted measured emission spectrum) in a calibration sample matrix to a corresponding spectrum of chemically pre-treated fuel samples (e.g., solvent-diluted fuel sample). In aspects where W is derived by comparing known marked fuel samples with known marked solvent solutions, replicates of the same marker-solvent spectrum can be paired with spectrally different fuel—marker spectra (e.g., owing to solvatochromism) that have the same nominal marker concentration. In such aspects, the resulting projection function (W) can transform similarly marked fuels that are nevertheless spectrally dissimilar, into the corresponding solvent-marker spectrum (e.g., corrected emission spectrum).

In an aspect, the method of fuel analysis as disclosed herein can comprise a step of determining the amount of fuel marker in the fuel sample from the corrected emission spectrum. Quantification of the fuel marker in the fuel sample can be achieved by using any suitable methodology, such as spectral integration or peak height analysis, owing to the corrected emission spectrum being a pure marker spectrum.

In some aspects, determining the amount of fuel marker in the fuel sample comprises a least square fitting of the corrected emission spectrum to an emission fluorescence spectrum of one or more marked solvent solutions comprising a known amount of fuel marker and a solvent. In other aspects, determining the amount of fuel marker in the fuel sample comprises partial least squares (PLS) regression.

In an aspect, the corrected emission spectrum can be compared to a library that includes a plurality of known emission spectra, wherein each of the plurality of known emission spectra is correlated to a known concentration of the particular fuel marker in the fuel sample.

In an aspect, the method of fuel analysis as disclosed herein can further comprise a step of determining adulteration of the fuel by comparing the amount of fuel marker in the fuel sample to a target amount of fuel marker, wherein the target amount of fuel marker is a known amount of fuel marker used to mark the fuel by a fuel supplier.

In an aspect, a method of determining adulteration of a fuel can be performed in the field (e.g., on location, direct detection, etc.). Determining adulteration of a fuel in the field can include testing at any location where a fuel can be found. Determining adulteration in the field can allow for rapid qualitative and/or quantitative assessment of the presence and/or amount of fuel marker in a fuel sample, for example via a portable fluorescence spectrometer.

In another aspect, a fuel sample can be collected from a first location (e.g., a gas station), and then transported to a second location (e.g., a laboratory) for further testing, e.g., determining adulteration, for example via a fluorescence spectrometer.

In an aspect, if fuel sample data (e.g., fuel marker amount) matches control data of the marked fuel (e.g., target amount of fuel marker), the fuel can be deemed to be unadulterated fuel. As will be appreciated by one of skill in the art, and with the help of this disclosure, the "matching" of the fuel sample data (e.g., fuel marker amount) with the control data of the marked fuel (e.g., target amount of fuel marker) has to be within experimental error limits for the fuel sample to be deemed unadulterated, and such experimental error limits are dependent on the particular analytical technique used (e.g., fluorescence spectroscopy), the analytical instrumentation used for the detection and analysis of the fuel marker, the processing of the measured data (e.g., measured emission spectrum), etc. The matching of data can include measuring a fuel marker amount to determine if the fuel has been diluted, by comparing the fuel marker amount with the target amount of fuel marker. Quantification of the fuel marker amount can indicate the extent of dilution by a potential adulterant.

In an aspect, if the fuel sample data does not match the control data of the fuel, the fuel can be deemed to be adulterated fuel. As will be appreciated by one of skill in the art, and with the help of this disclosure, the difference between the fuel sample data and the control data of the marked fuel has to fall outside of experimental error limits (e.g., the fuel sample data and the control data of the marked fuel do not match) for the sample to be deemed adulterated, and such experimental error limits are dependent on the particular analytical technique used (e.g., fluorescence spectroscopy), the analytical instrumentation used for the detection and analysis of the fuel marker, the processing of the measured data (e.g., measured emission spectrum), etc.

In an aspect, the amount of fuel marker in a fuel sample can be determined by using at least two different (e.g., independent) methods of fuel analysis; e.g., a first method of fuel analysis and a second method of fuel analysis, to yield a first determined amount of fuel marker and a second determined amount of fuel marker, respectively. In an aspects, the first method of fuel analysis is the method of fuel analysis as disclosed herein based on fluorescence spectroscopy and the projection function (W); and the second method of analysis can comprise, without limitation, fluorescence spectroscopy; fluorescence spectroscopy of chemically pre-treating the fuel samples; gas chromatography (GC); mass spectrometry (MS); ultraviolet (UV) spectroscopy; high-pressure liquid chromatography (HPLC); infrared (IR) spectroscopy; and the like; or combinations thereof In some aspects, the percentage difference between the first determined amount of fuel marker and the second determined amount of fuel marker can be in the range of from about ±5% to about ±10%, alternatively less than or equal to about 10%, 9%, 8%, 7%, 6%, or 5%.

In some aspects, the agreement between the first method of fuel analysis (e.g., method of fuel analysis as disclosed herein) and the second method of fuel analysis (e.g., fluorescence spectroscopy of chemically pre-treating the fuel samples) can be increased by equal to or greater than about 5%, 6%, 7%, 8%, 9%, or 10% via the disclosed method of fuel analysis relying on the projection function (W), based on the percentage difference in values obtained from a corresponding (e.g., like or identical) samples in the absence of chemical pre-treatment.

Generally, a fluorescence spectrometer comprises an excitation source, a sample holder (e.g., sample), and a detector. Fluorescence spectrometers rely on analyte (e.g., fuel marker) molecules absorbing excitation radiation (which can be measured in the form of an excitation spectrum) and emitting radiation (which can be measured in the form of an emission spectrum). The concentration of the analyte can be correlated to the intensity of the emission.

The excitation source (e.g., light source) can comprise a light-emitting diode (LED) and/or a laser diode. LEDs are available in a wide variety of wavelengths. An LED is a compact semiconductor device that emits light when electrical current is applied. The color (i.e., wavelength) of the emitted light depends on the composition of the semiconducting material used in the LED, and can be near-ultraviolet, visible, or infrared. LEDs have a compact size, low power consumption, minimal heat output, fast switching and adjusting properties, high emission stability and extremely long life span. Laser diodes emit monochromatic radiation, and can be easily focused and manipulated. The LEDs and/or a laser diodes can provide for portability of the spectrometer, owing to their relatively small size, as well as ease of temperature control. In an aspect, the fluorescence spectrometer comprises a temperature-controlled excitation source, such as a temperature-controlled LED and/or a temperature-controlled laser diode.

The sample or sample holder is generally not temperature-controlled. In a laboratory setting, the sample and sample holder generally are already at room temperature (e.g., the temperature of the surrounding environment), or are allowed to equilibrate before recording a fluorescence emission spectrum. The sample holders (e.g., samples) can be temperature-controlled in bench-top spectrometers, although the power consumption for controlling the temperature of the samples in fluorescence spectrometers render them impractical for portable devices.

The detector (e.g., optical detector) receives light emitted by the sample and provides the emission spectrum. Generally, fluorescence spectrometers can comprise photo-multiplier tubes as detectors, although charge-coupled devices (CCDs) can provide for portability of the spectrometer, owing to reduced size. CCDs typically contain 106 or more elements (e.g., 2048 elements). The CCD elements convert the photons of light received from the sample into an electrical signal, which is further translated into the emission spectrum. Each CCD element can independently accumulate charge as a function of its own light exposure. CCDs can display a non-linear element response with temperature variations, thereby introducing distortions in the shape of the emission spectrum. Detectors in fluorescence spectrometers can be temperature-controlled, although controlling the detector temperature leads to an increase need for available battery power in portable spectrometers.

In an aspect, the excitation source and/or the detector can be temperature-controlled by using any suitable methodology. For example, the excitation source and/or the detector can be temperature-controlled by using a thermo-electric cooling (TEC) temperature regulator. Generally, the TEC can be a Peltier device, which transfers heat from one side of the device to the other side against the temperature gradient based on the application of a DC voltage. The TEC or any other suitable temperature regulator is capable of heating the excitation source and/or the detector when the ambient temperature is low and is capable of cooling the excitation source and/or the detector when the ambient temperature is elevated.

For purposes of the disclosure herein, the term "temperature-controlled" refers to a temperature variation within about ±1° C., alternatively within about ±0.5° C., alternatively within about ±0.25° C., or alternatively within about ±0.1° C. of a target temperature (e.g., fixed temperature setting, such as a reference temperature, spectrometer temperature, etc.).

In an aspect, the fluorescence spectrometer as disclosed herein is a portable spectrometer. As would be appreciated by one of skill in the art, there are a variety of factors that can qualify an analytical instrument as "portable," including but not limited to: the portability of each and all components (i.e., both excitation source and detector have to be portable) of the spectrometer; size and weight of the spectrometer; energy input requirements; influence of environmental factors (e.g., temperature) on the instrument performance; detection limits and sensitivity to environmental factors, such as temperature (i.e., portable instruments notoriously display higher detection limits and lower sensitivity when compared to laboratory setting conditions); etc. Further, and as will be appreciated by one of skill in the art, and with the help of this disclosure, simply moving an analytical instrument such as a fluorescence spectrometer from a laboratory into field testing conditions does not render the analytical instrument portable. A portable device has to be capable of repeated sample analysis under field testing conditions while maintaining accuracy and precision measurement. For purposes of the disclosure herein, an instrument is considered portable if it substantially retains accuracy and/or precision of measurements under field-testing conditions (e.g., under variable temperatures); or alternatively if it improves accuracy and/or precision of measurements under field-testing conditions (e.g., under variable temperatures).

In an aspect, a method of fuel analysis as disclosed herein can comprise obtaining a measured emission spectrum, via fluorescence spectroscopy, from a fuel sample by utilizing a fluorescence spectrometer; wherein the fluorescence spectrometer comprises a detector and a temperature-controlled excitation source; wherein the fuel sample and the detector are not temperature-controlled; wherein the fuel comprises a fuel marker and a fuel matrix; wherein the measured emission spectrum comprises a first spectral component corresponding to type and amount of fuel marker in the fuel sample, a second spectral component corresponding to a spectral perturbation, and a third spectral component corresponding to fuel matrix fluorescence; and wherein the spectral perturbation comprises a temperature perturbation and/or a fuel matrix perturbation.

The fuel matrix perturbation comprises fuel matrix effects that induce spectral inconsistencies in similarly marked fuel samples, as disclosed herein. The fuel matrix perturbation can comprise solvatochromism, as disclosed herein.

The temperature perturbation comprises temperature effects that induce wavelength shift and/or bandwidth changes. As will be appreciated by one of skill in the art, and with the help of this disclosure, temperature variations can induce spectral changes in spectrum wavelength (e.g., wavelength shift) and/or bandwidth (e.g., bandwidth change), as well as spectrum intensity variations.

The method of fuel analysis as disclosed herein targets spectral changes owing to temperature variations (e.g., wavelength shift, bandwidth change, spectrum intensity variations), wherein such spectral changes can negatively impact the accuracy and precision of determining the concentration of fuel markers in fuels. In an aspect, the method of fuel analysis as disclosed herein can be applicable across a wide temperature range, e.g., from about −10° C. to about 60° C., alternatively from about 0° C. to about 50° C., or alternatively from about 5° C. to about 45° C. The method of fuel analysis employs a projection function (e.g., transformation matrix, projection function W) as disclosed herein for projecting the compromised matrix-perturbed spectral measurements onto a space that is solely described by a solvent-marker matrix, wherein the polar environment that the fuel marker is subjected to is fixed and wherein the main variation is from fuel marker dosing level. The correction of temperature effects on the emission spectrum can employ peak wavelength correction (e.g., peak wavelength correction of the measured emission spectrum to match that of a reference (solvent-marker) spectrum); baseline correction (e.g., spectrum deconvolution that removes a range of possible baseline shapes from the fuel-marker emission spectrum without distorting the marker spectrum); decoupling of the deconvoluted spectrum (e.g., correction of the spectrum with a pre-defined transformation matrix to achieve a matrix normalized spectra as previously described herein); spectrum intensity correction; etc.

In an aspect, the method of fuel analysis as disclosed herein can correct for temperature induced spectral changes by (i) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; and (ii) decoupling the deconvoluted measured emission spectrum to yield a corrected emission spectrum via a fuel matrix projection function, wherein the corrected emission spectrum comprises the first spectral component, and wherein the fuel matrix projection function orthogonally projects the deconvoluted measured emission spectrum onto a subspace devoid of at least a portion of the second spectral component to yield the corrected emission spectrum. The step of deconvoluting the measured emission spectrum and the step of decoupling the deconvoluted measured emission spectrum have been described in more detail previously herein.

In some aspects, the step of decoupling the deconvoluted measured emission spectrum can further comprise the removal of the temperature perturbation via the fuel matrix projection function. In such aspects, the subspace devoid of at least a portion of the second spectral component can be a subspace devoid of the fuel matrix perturbation, and optionally devoid of the temperature perturbation. The fuel matrix projection function can provide for the removal of multiplicative fuel matrix perturbation as disclosed herein. The fuel matrix projection function can further provide for the removal of the temperature perturbation (e.g., can further correct the spectrum for wavelength shift and/or bandwidth changes induced by temperature variations). The fuel matrix projection function can provide for spectra with bandwidths that match the marked solvent, thereby effectively normalizing (e.g., correcting for) bandwidth related temperature changes. Generally, the fuel matrix projection function does not substantially correct for fluorescence emission intensity variations (e.g., signal intensity variations), owing to the inability to define a transformation matrix that simultaneously corrects for fuel matrix differences and sample temperature, because both of these effects (e.g., fuel matrix differences and sample temperature) result in intensity variations. As will be appreciated by one of skill in the art, and with the help of this disclosure, the experimental design that would allow data generation where the both effects (e.g., fuel matrix differences and sample temperature) are not co-varying is challenging to implement in practice, and would significantly complicate the process of generating calibration samples for analysis.

In other aspects, the step of decoupling the deconvoluted measured emission spectrum can further comprise the removal of the temperature perturbation via a temperature projection function. In such aspects, the method of fuel analysis as disclosed herein can comprise the steps of (i) decoupling the deconvoluted measured emission spectrum to yield a temperature corrected emission spectrum via a temperature projection function, wherein the temperature corrected emission spectrum comprises the first spectral component and a portion of the second spectral component, and wherein the temperature projection function orthogonally projects the deconvoluted measured emission spectrum onto a subspace devoid of the temperature perturbation to yield the temperature corrected emission spectrum; and (ii) decoupling the temperature corrected emission spectrum to yield a corrected emission spectrum via a fuel matrix projection function, wherein the corrected emission spectrum comprises the first spectral component, and wherein the fuel matrix projection function orthogonally projects the temperature corrected emission spectrum onto a subspace devoid of the fuel matrix perturbation to yield the corrected emission spectrum.

The temperature projection function can be derived as disclosed herein for the fuel matrix projection function. For example, the temperature projection function can be derived by comparing emission fluorescence spectra of a marked fuel sample comprising a known amount of fuel marker; wherein the emission fluorescence spectra are recorded at two or more different temperatures; and wherein comparing emission fluorescence spectra comprises principal components regression analysis.

In an aspect, the method of fuel analysis as disclosed herein can correct the measured emission spectrum and/or the corrected emission spectrum for wavelength to yield a wavelength-corrected emission spectrum by matching peak wavelength with a reference fuel marker fluorescence emission wavelength. The peak wavelength correction to a reference wavelength can account for temperature related wavelength changes. As will be appreciated by one of skill in the art, and with the help of this disclosure, and without wishing to be limited by theory, the peak wavelength is known for a known fuel marker. Consequently, the wavelength axis of a spectrum (usually x-axis) can be shifted either towards higher wavelengths or lower wavelengths until the peak wavelength matches the known peak wavelength for the known fuel marker. The reference fuel marker fluorescence emission wavelength is the known fuel marker peak wavelength or emission wavelength. Matching peak wavelength with a reference fuel marker fluorescence emission wavelength can be regarded by one of skill in the art as a wavelength calibration. Further, and as will be appreciated by one of skill in the art, and with the help of this disclosure, matching peak wavelength with a reference fuel marker fluorescence emission wavelength does not alter the magnitude or intensity of the spectra signal; it only corrects for the wavelength where the fluorescence emission peak appears, by "sliding" the wavelength axis as necessary towards higher wavelengths or lower wavelengths until the peak wavelength matches the known peak wavelength for the known fuel marker.

In an aspect, the method of fuel analysis as disclosed herein can correct for the signal intensity variations that stem from temperature variations. The projection function and wavelength correction steps can provide for temperature resolved emission spectra for samples that are dosed (e.g., marked) with different concentrations of marker; wherein such temperature resolved emission spectra are sanitized of temperature driven wavelength and bandwidth variations, but with intensities that change as a function of sample temperature and concentration.

In order to separate the temperature driven intensity variation from the intensity change that is due to marker dosing levels, the method of fuel analysis as disclosed herein can correct for the signal intensity variations that stem from temperature variations by mathematically fitting normalized concentration estimates from temperature perturbed samples at a fixed concentration of marker, to temperature. The normalized concentration values can be estimated from the ratio of the concentration estimate (y) at a given temperature (e.g., sample temperature) to the concentration estimate ($y_r$) at a known (reference) temperature (e.g., 25° C.). $y_r$ values are derived from a solvent sample that is dosed (e.g., marked) with the fuel marker at known experimental concentrations.

The correction for temperature driven signal intensity variations yields fitting parameters that are generalizable across different marker dosing levels and across fuel types. $y/y_r$ is substantially independent of fuel marker concentration and fuel type. Consequently, in order to adjust the marker concentration estimate for temperature, it is necessary to know $y_r$ (i.e., the concentration estimate at the known reference temperature) and the sample temperature. The correction for temperature driven signal intensity variations is most effective if parameters are derived individually for each spectrometer. However, a significant level of correction can be observed with parameters generated from a reference spectrometer and applied to other spectrometers.

In an aspect, the method of fuel analysis as disclosed herein can further comprise the steps of (1) determining an apparent amount of fuel marker in the fuel sample at the fuel sample temperature; and (2) applying a correction factor (e.g., $y/y_r$) to the apparent amount of fuel marker in the fuel sample at the fuel sample temperature to yield a corrected amount of fuel marker in the fuel sample at a reference temperature. For purposes of the disclosure herein, the reference temperature is the temperature at which $y_r$ was determined. In some aspects, the reference temperature can be the temperature at which the excitation source and optionally the detector are controlled. For example, the reference temperature can be from about 15° C. to about 30° C., alternatively from about 20° C. to about 27.5° C., or alternatively from about 20° C. to about 25° C.

In an aspect, the sample is not temperature-controlled. However, the temperature of the sample can be monitored, such that the temperature of the sample is known at the time the measured emission spectrum is obtained. In an aspect, the temperature of the sample can be monitored by using any suitable methodology, for example by employing an infrared (IR) thermocouple.

The correction factor (e.g., $y/y_r$) correlates apparent known amounts of fuel marker in solvent with reference known amounts of fuel marker in solvent (e.g., marked solvent solution) across a temperature range. Nonlimiting examples of solvents suitable for forming marked solvent solutions as disclosed herein include aliphatic hydrocarbons, aromatic hydrocarbons, mesitylene (1,3,5-trimethylbenzene or TMB), petroleum distillates, halogenated aliphatic hydrocarbons, halogenated aromatic hydrocarbons, or combinations thereof. The fuel marker can be present in the marked solvent solutions in an amount of from about 0.1 ppb to about 1,000 ppb, alternatively from about 0.5 ppb to about 500 ppb, or alternatively from about 1 ppb to about 200 ppb, based on the total weight of the marked solvent solutions.

As will be appreciated by one of skill in the art, and with the help of this disclosure, the apparent amounts of fuel marker in a given solvent at a given temperature (e.g., sample temperature) are known, as they are calculated from the emission spectrum that has not been corrected for temperature driven signal intensity variations. y values can be recorded across a temperature range, and then can be divided by $y_r$ (which is recorded at the reference temperature) to yield the correction factor (e.g., $y/y_r$). In an aspect, the temperature range can be from about −10° C. to about 60° C., alternatively from about 0° C. to about 50° C., or alternatively from about 5° C. to about 45° C.

The correction factor (e.g., $y/y_r$) corrects for fluorescence emission intensity variations (e.g., signal intensity variations) induced by temperature variations. The correction factor (e.g., $y/y_r$) is fuel marker specific, i.e., the correction factor (e.g., $y/y_r$) is derived for each fuel marker.

In an aspect, the corrected amount of fuel marker in the fuel sample can be further used for determining adulteration of the fuel by comparing the corrected amount of fuel marker in the fuel sample to a target amount of fuel marker, wherein the target amount of fuel marker is a known amount of fuel marker used to mark the fuel by a fuel supplier.

In an aspect, the method of fuel analysis as disclosed herein that corrects for temperature driven spectral variations (e.g., wavelength shift, bandwidth changes, intensity changes) can be advantageously characterized by improved precision and/or accuracy when compared to the precision and/or accuracy of an otherwise similar method of fuel analysis that does not employ the temperature correction methods as disclosed herein (e.g., projection function, correction factor, wavelength correction). Generally, accuracy refers to the closeness of a result (e.g., measurement result, measured concentration) to the true value (e.g., standard value, known value); and precision refers to the closeness of two or more results (e.g., measurement results, measured concentrations) to each other.

In an aspect, the precision of the corrected amount of fuel marker can be increased by equal to or greater than about 50%, alternatively equal to or greater than about 60%, or alternatively equal to or greater than about 70% when compared to the precision of the amount of fuel marker determined by an otherwise similar method of fuel analysis that does not employ a projection function and/or a correction factor.

In an aspect, the accuracy of the corrected amount of fuel marker is increased by equal to or greater than about 5%, alternatively equal to or greater than about 10%, or alternatively equal to or greater than about 15% when compared to the accuracy of the amount of fuel marker determined by an otherwise similar method of fuel analysis that does not employ a projection function and/or a correction factor.

In an aspect, a method of fuel analysis as disclosed herein can comprise the steps of (a) acquiring a fuel sample; (b) determining the presence of a fuel marker in the fuel sample; (c) obtaining a measured emission spectrum, via fluorescence spectroscopy, from a fuel sample by utilizing a portable fluorescence spectrometer; wherein the fluorescence spectrometer comprises a detector and a temperature-controlled excitation source; wherein the fuel sample and the detector are not temperature-controlled; wherein the fuel comprises a fuel marker and a fuel matrix; wherein the measured emission spectrum comprises a first spectral component corresponding to type and amount of fuel marker in the fuel sample, a second spectral component corresponding to a spectral perturbation, and a third spectral component corresponding to fuel matrix fluorescence; wherein the spectral perturbation comprises a temperature perturbation and a fuel matrix perturbation; wherein the fuel matrix perturbation comprises fuel marker solvatochromism; and wherein the temperature perturbation comprises wavelength shift and/or bandwidth changes; (d) correcting the measured emission spectrum for wavelength to yield a wavelength-corrected measured emission spectrum by matching peak wavelength with a reference fuel marker fluorescence emission wavelength; (e) deconvoluting the wavelength-corrected measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; (f) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum; (g) determining an apparent amount of fuel marker in the fuel sample at the fuel sample temperature from the corrected emission spectrum; (h) applying a correction factor to the apparent amount of fuel marker in the fuel sample at the fuel sample temperature to yield a corrected amount of fuel marker in the fuel sample at a reference temperature; and (i) determining adulteration of the fuel by comparing the corrected amount of fuel marker in the fuel sample to a target amount of fuel marker, wherein the target amount of fuel marker is a known amount of fuel marker used to mark the fuel by a fuel supplier. In such aspect, the precision of the corrected amount of fuel marker can be increased by equal to or greater than about 50% when compared to the precision of the amount of fuel marker determined by an otherwise similar method of fuel analysis that does not employ a projection function and/or a correction factor. In such aspect, the accuracy of the corrected amount of fuel marker is increased by equal to or greater than about 5% when compared to the accuracy of the amount of fuel marker determined by an otherwise similar method of fuel analysis that does not employ a projection function and/or a correction factor.

In an aspect, a method of spectra correction as disclosed herein can comprise a step of placing a fuel sample in a fluorescence spectrometer; wherein the fluorescence spectrometer comprises a temperature-controlled detector and a temperature-controlled excitation source; wherein the temperature-controlled detector and the temperature-controlled excitation source are characterized by a spectrometer temperature; wherein the fuel sample is not temperature-controlled; wherein the fuel sample is characterized by a sample temperature, and wherein the sample temperature is different from the spectrometer temperature; wherein the fuel comprises a fuel marker; wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively. While the present disclosure is discussed in detail in the context of a method of spectra correction wherein the temperature of the detector and the temperature of the excitation source are controlled to the same reference temperature (e.g., spectrometer temperature), it should be understood that such method or any steps thereof can be applied to a method of spectra correction wherein the temperature of the detector and the temperature of the excitation source are controlled to the different temperatures.

Further, while the present disclosure is discussed in detail in the context of a method of spectra correction for determining adulteration of a fuel by using a fluorescence spectrometer, it should be understood that such method or any steps thereof can be applied for spectra correction of spectra obtained by using any other suitable type of spectrometer. For example, a method of spectra correction as disclosed herein can comprise a step of placing a sample in a spectrometer; wherein the spectrometer comprises a temperature-controlled detector and a temperature-controlled excitation source; wherein the temperature-controlled detector and the temperature-controlled excitation source are characterized by a spectrometer temperature; wherein the sample is not temperature-controlled; wherein the sample is characterized by a sample temperature, and wherein the sample temperature is different from the spectrometer temperature; wherein the sample comprises an analyte; wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively. The sample can comprise a fuel sample as disclosed herein, or any other suitable sample. The analyte can comprise a fuel marker as disclosed herein, or any other suitable analyte. The spectrometer can comprise a fluorescence spectrometer as disclosed herein, or any other suitable spectrometer that has an excitation source, a sample (e.g., sample holder), and a detector.

In aspects where both the detector and the excitation source are temperature-controlled and the sample is not temperature-controlled, the time period that takes for the sample temperature to equilibrate to the spectrometer temperature (e.g., equilibration time period) can be inconvenient, as it reduces the number of samples that can be analyzed by a given spectrometer in a given time period. As will be appreciated by one of skill in the art, and with the help of this disclosure, because the sample is often measured in a glass receptacle (e.g., glass cuvette) with poor heat transfer dynamics, the time period it takes for the sample temperature to sync up (e.g., equilibrate) to the spectrometer temperature (e.g., equilibration time period) can often be longer than expected and could be longer still if the temperature differential between the sample and the spectrometer was significant.

In an aspect, a method of spectra correction as disclosed herein can adjust (e.g., correct) the sample emission intensity (e.g., signal intensity) for temperature variations by predicting the expected emission intensity (e.g., expected signal intensity) of the sample at the detector (reference) temperature (e.g., spectrometer temperature) using a few repeat measurements (e.g., two or more measurements). In such aspect, the method of spectra correction as disclosed herein can allow for skipping (e.g., by-passing) the often lengthy and variable waiting period (e.g., equilibration time period) necessary to fully synch the sample and spectrometer temperature. The method of spectra correction as disclosed herein can take advantage of the exponential growth or decay of the emission intensity (e.g., signal intensity) with time as the sample equilibrates with the spectrometer temperature (e.g., target temperature, machine temperature, device temperature) from a temperature (e.g., sample temperature) that is higher or lower, respectively than the spectrometer temperature.

In an aspect, a method of spectra correction as disclosed herein can comprise a step of acquiring, via the fluorescence spectrometer, two or more measured emission spectra of the fuel sample during the first half of the equilibration time period. The two or more measured emission spectra can comprise 2, 3, 4, 5, 6 or more measured emission spectra. In an aspect, a method of spectra correction as disclosed herein can comprise a step of acquiring, via the fluorescence spectrometer, 3 measured emission spectra of the fuel sample during the first half of the equilibration time period. As will be appreciated by one of skill in the art, and with the help of this disclosure, the method of spectra correction as disclosed herein does not acquire emission spectra until the sample temperature equilibrates to the spectrometer temperature; the method of spectra correction as disclosed herein acquires emission spectra during a short time period at the beginning of the equilibration time periods (e.g., during the first half of the equilibration time period), which advantageously and significantly shortens the time necessary to analyze a sample (e.g., fuel sample) and evaluate the concentration of the analyte (e.g., fuel marker) in the sample.

In an aspect, the measured emission spectra can be acquired in a time period that is less than about 50% (i.e., half), alternatively less than about 40%, alternatively less than about 30%, alternatively less than about 25%, alternatively less than about 20%, alternatively less than about 15%, alternatively less than about 10%, or alternatively less than about 5% of the equilibration time period. As will be appreciated by one of skill in the art, and with the help of this disclosure, the amount of analyte (e.g., fuel marker) in the sample (e.g., fuel sample) may or may not be determined during the first half of the equilibration time period. For example, the data acquired from the spectrometer can be processed in real-time and the amount of analyte (e.g., fuel marker) in the sample (e.g., fuel sample) can be determined about concurrently with acquiring the measured emission spectra. As another example, the data acquired from the spectrometer can be stored and the amount of analyte (e.g., fuel marker) in the sample (e.g., fuel sample) can be determined at later time. However, regardless of when the data is processed to determine the amount of analyte (e.g., fuel marker) in the sample (e.g., fuel sample), the data is acquired during the first half of the equilibration time period.

In some aspects, the amount of fuel marker in the fuel sample can be determined over a time period that is less than about 50%, (i.e., half), alternatively less than about 40%, alternatively less than about 30%, alternatively less than about 25%, alternatively less than about 20%, alternatively less than about 15%, alternatively less than about 10%, or alternatively less than about 5% of the equilibration time period. In some aspects, the amount of fuel marker in the fuel sample can be determined at the beginning of the time equilibration time period; for example during the first about 50%, (i.e., half), alternatively about 40%, alternatively about 30%, alternatively about 25%, alternatively about 20%, alternatively about 15%, alternatively about 10%, or alternatively about 5% of the equilibration time period.

In an aspect, a method of spectra correction as disclosed herein can comprise a step of deriving a signal intensity corresponding to the fuel marker from each measured emission spectrum. In an aspect, the step of deriving a signal intensity corresponding to the fuel marker from each measured emission spectrum is spectrometer specific.

In some aspects, the signal intensity can comprise the peak height. In other aspects, the signal intensity can comprise the area under the peak curve. The terms "peak height" and "area under the curve" or "area under the peak curve" are known to one of skill in the art.

As disclosed herein, each measured emission spectrum can comprise a first spectral component corresponding to type and amount of fuel marker in the fuel sample, a second spectral component corresponding to a spectral perturbation (e.g. temperature perturbation and/or a fuel matrix perturbation), and a third spectral component corresponding to fuel matrix fluorescence.

In an aspect, deriving the signal intensity corresponding to the fuel marker from each measured emission spectrum can comprise (1) deconvoluting each measured emission spectrum to yield a deconvoluted measured emission spectrum, wherein deconvoluting each measured emission spectrum comprises the removal of the third spectral component from the measured emission spectrum to yield the deconvoluted measured emission spectrum, and wherein the deconvoluted measured emission spectrum comprises the first spectral component and the second spectral component; (2) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of at least a portion of the second spectral component to yield the corrected emission spectrum; and (3) determining the signal intensity corresponding to the fuel marker from the corrected emission spectrum; as disclosed herein. As disclosed herein, the projection function (e.g., temperature projection function and/or fuel matrix projection function) is fuel marker specific.

In an aspect, a method of spectra correction as disclosed herein can comprise a step of generating a signal intensity variation over time curve and a sample temperature variation over time curve, wherein the signal intensity decreases with the sample temperature increasing over time or increases with the sample temperature decreasing over time; and wherein the signal intensity decrease or increase follows an exponential decay or growth curve over time, respectively. In an aspect, the step of generating a signal intensity variation over time curve and a sample temperature variation over time curve is spectrometer specific.

In aspects where the sample temperature is lower than the spectrometer temperature, the temperature of the sample increases to equilibrate to the spectrometer temperature, and the emission intensity (e.g., signal intensity) decays while the sample temperature increases. In such aspects, the emission intensity (e.g., signal intensity) decays according to equation (6):

$$y_1 = c_1 + a_1 \exp^{\left(\frac{x}{\tau_1}\right)} \quad (6)$$

wherein x is the time, $y_1$ is the emission intensity (e.g., signal intensity), $\tau_1$ is the decay constant, $c_1$ is the offset value, and $a_1$ is the amplitude value (e.g., y at x=0).

In aspects where the sample temperature is greater than the spectrometer temperature, the temperature of the sample decreases to equilibrate to the spectrometer temperature, and the emission intensity increases following an exponential growth curve while the sample temperature decreases. In such aspects, the emission intensity (e.g., signal intensity) follows an exponential growth curve according to equation (7):

$$-y_2 = -c_2 - a_2 \exp^{(-x_2)} \quad (7)$$

wherein $y_2$ is the emission intensity (e.g., signal intensity), $\tau_2$ is the growth constant, $c_2$ is the offset value, and $a_2$ is the amplitude value. As will be appreciated by one of skill in the art, and with the help of this disclosure, and without wishing to be limited by theory, offset values are the steady-state values of the curves (e.g., exponential growth or decay curves).

Without wishing to be limited by theory, because of the inverse proportionality relationship between fluorescence emission intensity (e.g., signal intensity) and sample temperature, the emission decay or growth is mirrored by the opposite trend in sample temperature, such that when the sample emission intensity (e.g., signal intensity) is growing with time, the sample temperature is decaying at the same rate and vice versa (when the sample emission intensity is decaying with time, the sample temperature is growing at the same rate). Consequently, and without wishing to be limited by theory, equations (6) and (7) can be interchangeably applied to sample temperature and sample emission intensity (e.g., signal intensity) depending on whether the spectrometer temperature is lower (equation (6) can be applied to the sample emission intensity and equation (7) can be applied to the sample temperature) or higher (equation (6) can be applied to the sample temperature and equation (7) can be applied to the sample emission intensity) than the sample temperature.

For purposes of the disclosure herein, the growth and decay rates are assumed to be equivalent. For example, when the sample emission intensity (e.g., signal intensity) is growing with time at a certain rate, the sample temperature is decaying at the same rate at which the sample emission intensity (e.g., signal intensity) is growing with time. As another example, when the sample emission intensity (e.g., signal intensity) is decaying with time at a certain rate, the sample temperature is growing at the same rate at which the sample emission intensity (e.g., signal intensity) is decaying with time. In some aspects, the temperature growth constant is equivalent to the signal intensity decay constant; wherein the temperature growth constant is the inverse function of the signal intensity decay constant. In other aspects, the signal intensity growth constant is equivalent to the temperature decay constant; wherein the signal intensity growth constant is the inverse function of the temperature decay constant. By assuming that the growth and decay rates (e.g., the growth and decay constants) are equivalent, for two fixed time points $x_1$ and $x_2$, the following expression can be derived according to equation (8):

$$\tau_1 \tau_2 = \frac{\ln\left(\frac{A_1 + c_a}{A_2 + c_a}\right)}{\ln\left(\frac{B_1 + c_b}{B_2 + c_b}\right)} \quad (8)$$

wherein $c_a$ and $c_b$ are the offset parameters from the growth and decay curves, respectively; wherein $A_1$ and $A_2$ are the amplitude values for the growth curve at times $x_1$ and $x_2$, respectively; and wherein $B_1$ and $B_2$ are the amplitude values for the decay curve at times $x_1$ and $x_2$, respectively. As will be appreciated by one of skill in the art, and with the help of this disclosure, and without wishing to be limited by theory, the method of spectra correction as disclosed herein assumes that real-time sample temperature measurements are available (which may be obtained for example by a judiciously placed infrared thermometer, such as an IR thermocouple). Consequently, all the parameters pertaining to the temperature decay or growth curves are also known; including $c_a$ or $c_b$, respectively, which is the positive or negative difference between the initial sample temperature and the spectrometer temperature, and which depends on the magnitude of the initial sample temperature relative to the spectrometer temperature).

In an aspect, a method of spectra correction as disclosed herein can comprise a step of estimating a signal intensity corresponding to the fuel marker at the end of the equilibration time period. In an aspect, the step of estimating the signal intensity corresponding to the fuel marker at the end of the equilibration time period is spectrometer specific. The expression according to equation (8) can be used to derive the following function according to equation (9):

$$\left\| \tau_1 \tau_2 - \frac{\ln\left(\frac{A_1'}{A_2'}\right)}{\ln\left(\frac{B_1+C}{B_2+C}\right)} \right\| \tag{9}$$

wherein $A_1'=(A_1+c_a)$; wherein $A_2'=(A_2+c_a)$; and wherein C is the estimated offset between the intensity from a sample whose temperature is t (wherein the sample temperature t is different than the equilibration temperature or spectrometer temperature $t_{ref}$) and the intensity of the same sample after it has equilibrated to the spectrometer temperature $t_{ref}$ (which is the steady-state signal intensity or emission intensity corresponding to $t_{ref}$). The offset C is determined by the least squares minimization of the function according to equation (9).

In an aspect, a method of spectra correction as disclosed herein can comprise a step of determining the amount of fuel marker in the fuel sample from the estimated signal intensity corresponding to the fuel marker at the end of the equilibration time period.

In an aspect, the amount of fuel marker in the fuel sample determined from the estimated signal intensity corresponding to the fuel marker at the end of the equilibration time period can be further used for determining adulteration of the fuel by comparing the amount of fuel marker in the fuel sample to a target amount of fuel marker, wherein the target amount of fuel marker is a known amount of fuel marker used to mark the fuel by a fuel supplier.

In an aspect, the precision of the method of spectra correction as disclosed herein can be maintained within about ±10%, alternatively within about ±7.5%, alternatively within about ±5%, alternatively within about ±2.5%, or alternatively within about ±1% of the precision of an otherwise similar method that calculates the signal intensity subsequent to the sample equilibrating to the spectrometer temperature (i.e., at the end of the equilibration time period).

In an aspect, the accuracy of the method of spectra correction as disclosed herein can be maintained within about ±10%, alternatively within about ±7.5%, alternatively within about ±5%, alternatively within about ±2.5%, or alternatively within about ±1% of the precision of an otherwise similar method that calculates the signal intensity subsequent to the sample equilibrating to the spectrometer temperature (i.e., at the end of the equilibration time period).

In an aspect, a method of fuel analysis employing spectra correction as disclosed herein can comprise the steps of (a) acquiring a fuel sample; (b) determining the presence of a fuel marker in the fuel sample; (c) placing the fuel sample in a portable fluorescence spectrometer; wherein the fluorescence spectrometer comprises a temperature-controlled detector and a temperature-controlled excitation source; wherein the temperature-controlled detector and the temperature-controlled excitation source are characterized by a spectrometer temperature; wherein the fuel sample is not temperature-controlled; wherein the fuel sample is characterized by a sample temperature, and wherein the sample temperature is different from the spectrometer temperature; wherein the fuel comprises a fuel marker and a fuel matrix; wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively; (d) acquiring, via the fluorescence spectrometer, three measured emission spectra of the fuel sample during the first half of the equilibration time period; (e) deriving a signal intensity corresponding to the fuel marker from each measured emission spectrum; (f) generating a signal intensity variation over time curve and a sample temperature variation over time curve, wherein the signal intensity decreases with the sample temperature increasing over time or increases with the sample temperature decreasing over time; and wherein the signal intensity decrease or increase follows an exponential decay or growth curve over time, respectively; (g) estimating a signal intensity corresponding to the fuel marker at the end of the equilibration time period; (h) determining the amount of fuel marker in the fuel sample from the estimated signal intensity corresponding to the fuel marker at the end of the equilibration time period; and (i) determining adulteration of the fuel by comparing the amount of fuel marker in the fuel sample to a target amount of fuel marker, wherein the target amount of fuel marker is a known amount of fuel marker used to mark the fuel by a fuel supplier.

In an aspect, the method of fuel analysis as disclosed herein can advantageously display improvements in one or more characteristics, when compared to similar methods of fuel analysis that lack a projection function (W) as disclosed herein. Generally, conventional methods of fuel analysis that lack a projection function (W) suffer from complex interactions between fuel markers and fuel, which require the use of rather complex quantitative fuel-marker models to estimate marker concentration levels (ppb) in fuel. Further, a vastly variable global pool of fuel matrices means that conventional methods of analysis that lack a projection function (W) as disclosed herein have to be tailored to specific needs in specific geographies, otherwise such methods quickly become ineffective. Furthermore, the difficult logistics of sourcing fuels with which to create "standards" for conventional methods of analysis that lack a projection function (W) as disclosed herein often lead to not having enough samples to create an effective analysis method. Changes in fuel formulations (legal and illegal) over time can lead to conventional methods of analysis that lack a projection function (W) as disclosed herein having the need to be continuously adjusted and refined to maintain performance.

In an aspect, the method of fuel analysis as disclosed herein can advantageously display the ability to process virtually any type of fuel sample comprising a fuel and a fuel marker of the type disclosed herein, irrespective of the quality of the fuel sample. The method of fuel analysis as disclosed herein can advantageously display enhanced sensitivity and accuracy of fuel marker analysis in complicated fuel matrices. The method of fuel analysis employing a projection function (W) as disclosed herein can advantageously simplify fuel samples spectra without the need to chemically pre-treat the analyzed fuel samples. The method of fuel analysis employing a projection function (W) as disclosed herein conveys a robust analysis method that can be used for spectrum decoupling of complex and diverse fuel samples (e.g., complex and diverse fuel marker—fuel matrix mixtures). The method of fuel analysis employing a projection function (W) as disclosed herein can advantageously transform measured emission spectra of fuel samples into generic pure fuel marker spectra from which fuel marker amounts (e.g., concentrations, levels) can be accurately estimated or calculated.

In an aspect, the method of fuel analysis as disclosed herein can advantageously be employed as a fuel marker specific global or universal quantitative model, which would conventionally be problematic due to the highly variable pool of fuel formulations. The projection function (W) can be derived by using experimental data accounting for really poor quality fuels (e.g., fuels distributed in severely impoverished parts of the world, such as third world countries), as well as high quality fuels (e.g., fuels distributed in first world countries, U.S., E.U., etc.), and as such the projection function can advantageously correct for spectral perturbations of any quality fuel. In an aspect, the method of fuel analysis as disclosed herein can advantageously be used on a global scale, and is fuel matrix independent.

In an aspect, the method of fuel analysis as disclosed herein can advantageously provide for faster analysis of fuel samples, by reducing or eliminating the need to chemically pre-treat fuel samples; which additionally can provide cost-savings both in terms of time and materials. The method of fuel analysis employing a projection function (W) as disclosed herein provides for mathematical dilution of the fuel samples that mimics the effect of solvent dilution, which corrects for fuel matrix effects via chemical pre-treatment of fuel samples.

In an aspect, the method of fuel analysis as disclosed herein can advantageously reduce the cost of generating and deploying fuel-marker models by facilitating the use of a single quantitative marker model for each fuel marker, across a spectrally and compositionally variable population of fuels from equally variable geographical sources and refined under variable processes, that is based on solvent not fuel.

In an aspect, the method of fuel analysis as disclosed herein can advantageously correct for temperature effects, such as variations in spectrum shape and intensity. As will be appreciated by one of skill in the art, and with the help of this disclosure, CCD detectors can lead to a distorted spectrum shape when the temperature of the detector changes, owing to a non-linear CCD element response to temperature. The method of fuel analysis as disclosed herein can advantageously correct for spectrum shape distortions, such as spectrum shape distortions owed to CCD detectors that are not temperature controlled.

In an aspect, the method of fuel analysis as disclosed herein can advantageously provide for a portable fluorescence spectrometer that not only retains precision and accuracy, but displays an increase in precision and accuracy owing to the methods of correcting for temperature effects as disclosed herein. The method of fuel analysis as disclosed herein can advantageously allow for the use of a spectrometer that does not control the temperature of the sample and optionally the detector, thereby reducing the power consumption requirements of a portable spectrometer, which in turn reduces the size and cost of the battery necessary for powering the spectrometer.

In an aspect, the method of spectra correction as disclosed herein can advantageously reduce the time necessary for acquiring the emission spectra by enabling the estimation of signal intensity prior to the sample equilibrating to the spectrometer temperature, wherein the sample is not temperature-controlled. Additional advantages of the method of fuel analysis and/or spectra correction as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

A laboratory-based study on several fuel samples collected from the field was conducted to investigate the method of fuel analysis comprising a projection function (W) as disclosed herein, wherein W orthogonally projects measured emission spectra onto a subspace devoid of spectral perturbations such as solvatochromism to yield corrected emission spectra. The fuels were marked with LSX markers. LSX refers to a device platform commercially available from Authentix. LSX employs laser-induced fluorescence spectroscopy to measure marking compounds in a variety of liquids.

The method of fuel analysis employing a projection function (W) as disclosed herein was compared with a method of fuel analysis employing chemically pre-treating fuel samples with a homogeneity inducing material. The fuel samples were Ghanaian gasoline samples.

21 gasoline blends obtained from Ghana were dosed with LSX187, a fluorescence fuel marker that is particularly susceptible to solvatochromism. Each fuel sample was dosed with 12.5 ppb, 25 ppb, 40 ppb, 50 ppb and 60 ppb of LSX187. A subset of the gasoline samples that were marked at 12.5 ppb and 25 ppb and all of the gasoline samples that were marked at 40 ppb were also dosed with "fuel premix," which is a common fuel adulterant in Ghana that is nevertheless known to boost the fluorescence emission of this particular fluorescence marker (LSX187). As will be appreciated by one of skill in the art, and with the help of this disclosure, the amount of premix adulterant in the fuel is inversely proportional to the boost in fluorescence emission, so that the recorded signal intensity of the 12.5 ppb marked samples is larger than the recorded signal intensity of the 40 ppb marked samples. All of the marked fuel samples were separated into 2 equal portions (e.g., halves) as follows. One portion of each sample was chemically pre-treated with 1,3,5-trimethylbenzene (TMB; mesitylene) solvent, by diluting the marked sample with solvent at a ratio of 7.33 to 1 (i.e., 0.75 mL of marked fuel to 4.75 mL of TMB). Using fluorescence emission spectra generated from the samples on a LSX3000 analyzer (SN: Beta004), a partial least squares (PLS) model that fits the fluorescence emission spectra from the chemically pre-treated samples to the marker concentration, was generated. A separate set of 8 gasoline samples that were not included in the model was used for validating the model. The 8 samples were marked and treated in the same manner as the calibration samples. FIG. 1A shows spectra recorded for from 21 untreated samples, each dosed with LSX187 from 12.5 ppb to 60 ppb. FIG. 1A displays significant spectral variation from matrix solvatochromism. FIG. 1B shows spectra that were recorded for chemically pre-treated samples. FIG. 1C shows the spectra from 1A that have been subjected to the method of fuel analysis employing a projection function (W) as disclosed herein, wherein a mathematical correction was performed as described previously herein according to equations (3), (4), and (5). FIGS. 1B and 1C display a reduction in spectrum scatter and a clear delineation of fuel marker concentration levels relative to FIG. 1A. FIGS. 1B and 1C display enhanced intensity levels of 12.5 ppb, 25 ppb and 40 ppb marked samples containing premix adulterant when compared to the samples with 50 ppb and 60 ppb fuel marker that did not contain premix adulterant.

LSX3000 measurements from chemically pre-treated independent validation samples (8 samples) were applied to the PLS model that was generated from the data in FIG. 1B. The results were compared against model estimates from sample spectra that were mathematically corrected for fuel matrix effects using the projection function (W) that was developed from fitting the data in FIG. 1A to the data in FIG. 1B. In generating the projection function (W), the factor space dimensions (columns) in $P_1$ and $P_2$ from equation (3) were set to 30 and 8, respectively. As will be appreciated by one of skill in the art, and with the help of this disclosure, the factor space dimensions are a and b, as previously described herein. The data in FIGS. 1A and 1B was generated from 40 validation samples (8 gasolines fuels at 5 marker concentration levels per fuel). The results are summarized in Table 1 and FIG. 2. Table 1 displays mathematical model estimates (via projection function W) from chemically pre-treated samples (e.g., chemically treated samples) in FIG. 1B versus sample measurements in FIG. 1A that were transformed using the proposed orthogonal correction method to yield the data in FIG. 1C. The mean and standard deviations at each concentration were generated from 8 samples that were independent of the calibration model.

level of confidence, which further suggests that while either approach (e.g., chemical pre-treatment and/or orthogonal projection via W) may be deployed for fuel testing, the method of analysis employing orthogonal projection via W can produce savings in terms of time, instrument usage, materials, etc. Fearn's criterion is described in more detail in "Comparing standard deviations," Tom Fearn, NIR News, volume 7, No 5, pp 5-6, 1996; which is incorporated by reference herein in its entirety.

The data in FIGS. 1A-1C, and 2, as well as Table 1 demonstrate the equivalence of the proposed correction method (e.g., method of analysis employing orthogonal projection via W) and the chemical pre-treatment of fuel samples with respect to fuel marker quantitation. The proposed method can simplify the LSX analysis workflow because it uses a single parameter W (n×n transformation matrix, where n is the number of wavelength channels in the emission spectrum) to implement the correction, while reducing or eliminating the need for field sample test kits used for pre-treating fuel samples prior to fluorescence measurements (e.g., LSX measurements). The corrected emission spectra produced with the method of analysis employing orthogonal projection via W is equivalent to the emission spectra of chemically pre-treated samples.

Example 2

The measured emission spectra of from samples containing a fluorescent fuel marker were processed with three different analysis methods, as follows. The measured emission spectra of fuel samples collected over 1 year were recorded with 31 LSX units for a total number of 29,057 LSX measurements, wherein 9,434 measurements were performed for gasoline samples, 17,338 measurements were performed for Diesel samples, and 2,285 measurements were performed for gasoil samples. The measured emission spectra of fuel samples were collected from a field location (Serbia), which will be referred to herein as a "model deployment location" or "model test location." The test fuels were marked with 100 ppb of LSX202 at a 100% dosing level. For all samples used with the 3 test models, additive

TABLE 1

| Sample Concentration (ppb) | Mean concentration estimate from chemically treated samples (ppb) | Standard deviation of concentration estimates from chemically treated samples (ppb) | Mean concentration estimates from mathematically corrected samples (ppb) | Standard deviation of concentration estimates from mathematically corrected samples (ppb) |
| --- | --- | --- | --- | --- |
| 0 | 0.5 | 0.8 | 0.6 | 0.7 |
| 12.5 | 13.0 | 1.2 | 12.3 | 1.1 |
| 25 | 25.6 | 2.4 | 24.4 | 1.5 |
| 50 | 52.2 | 3.5 | 49.2 | 3.1 |
| 60 | 64.9 | 1.7 | 59.8 | 4.2 |

Figure 2:
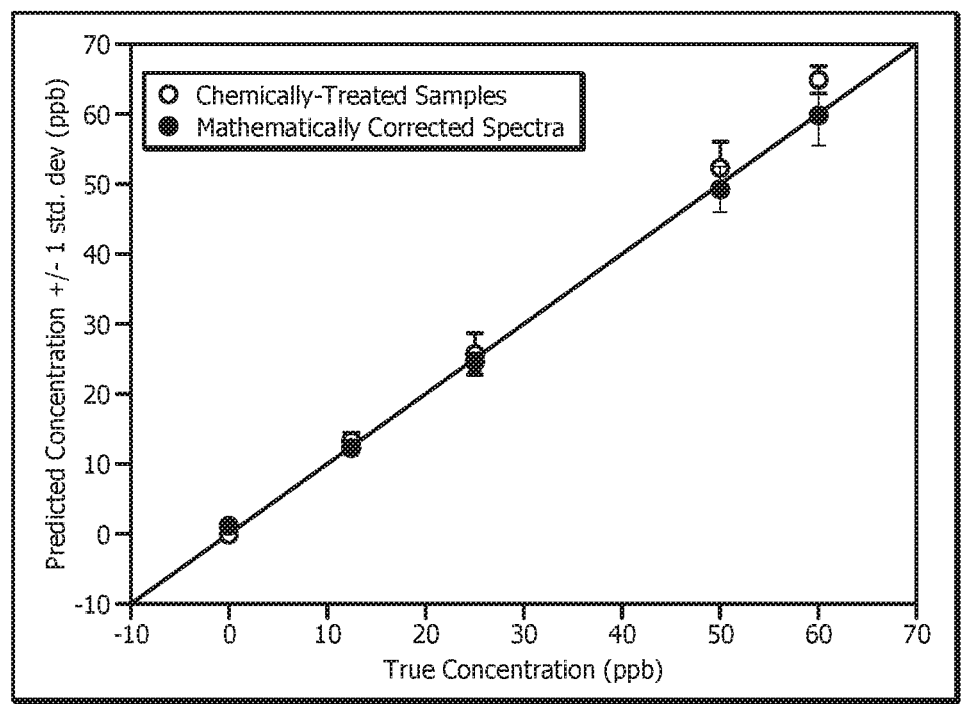
FIG. 2 displays a plot of data from Table 1 of Example 1.

Even though the precision of the mathematically corrected spectra at each concentration is relatively slightly poorer than the measurement precision from chemically pre-treated samples (FIGS. 1C and 1B, respectively), the impact on marker quantitation is negligible as shown in FIG. 2 and Table 1, likely because of the PLS model robustness to low levels of spectral measurement imprecision.

Fearn's criterion was used to compare the bias and standard deviations of the prediction errors derived from the two validation sample treatments (i.e., chemical pre-treatment and orthogonal projection via W). The comparison indicates that the differences are not significant at the 95% fuel fluorescence baseline from measured fuel sample spectra was removed via deconvolution to yield deconvoluted measured emission spectra as previously described herein.

For test model #1, the measured emission spectra were analyzed with a quantitative calibration model derived from fuel samples that were sourced from the model deployment (test) location. Consequently, the spectra from the calibration and test locations are spectrally similar. The data for test model #1 was processed with a basic LSX algorithm that utilizes partial least squares (PLS) regression to correlate fluorescence emission measurements across a fixed wavelength window to marker concentration. Additional spectral processing prior to quantitative marker evaluation is specific to what is required by the PLS method.

For test model #2, the measured emission spectra were analyzed with a quantitative calibration model derived from fuel samples that were sourced from a location that is different from the model deployment (test) location. The spectral variation/mismatch between the calibration fuels and the test fuels was significant. The data for test model #2 was processed with same basic LSX algorithm that was used in test model #1.

For test model #3, the measured emission spectra from the model deployment (test) location were analyzed with a generic marker-solvent model. The model was applied to test samples that were subject to the additive and multiplicative correction method disclosed herein, i.e., spectrum deconvolution followed by emission correction via orthogonal projection (i.e., method of fuel analysis employing a projection function (W) as disclosed herein). The projection function (W) was developed from marked fuel samples that were sourced from a location that is different from the model deployment (test) location. W was estimated by comparing marked fuel samples to marked solvent spectra as previously described herein, wherein W orthogonally projects measured emission spectra onto a subspace devoid of spectral perturbations such as solvatochromism to yield corrected emission spectra.

For test model #3 the multiplicative fuel matrix signature was removed from the baseline corrected spectra (e.g., deconvoluted measured emission spectra) using a mathematical approach to fuel matrix regulation (e.g., mathematical dilution). Mathematical dilution parameters were generated from Ghana fuel samples marked with 0-100 ppb LSX202 [~500 spectral scans].

For all test samples that were applied to test models #1 and #2, the fuel marker concentration estimates were derived from a partial least squares (PLS) model with no specialized spectral pre-preprocessing beyond that which is required by this quantitative analysis method. For test model #3, the pure component marker signature resulting from baseline line correction and the mathematical regulation of the fuel matrix was quantified by a least-squares fit to solvent/marker spectra [implemented with look-up table]. Marker concentration estimation with a solvent/marker quantitative model [using any number of mathematical data processing methods including PLS regression or a simple area-under the curve model], is also possible.

Figure 3:
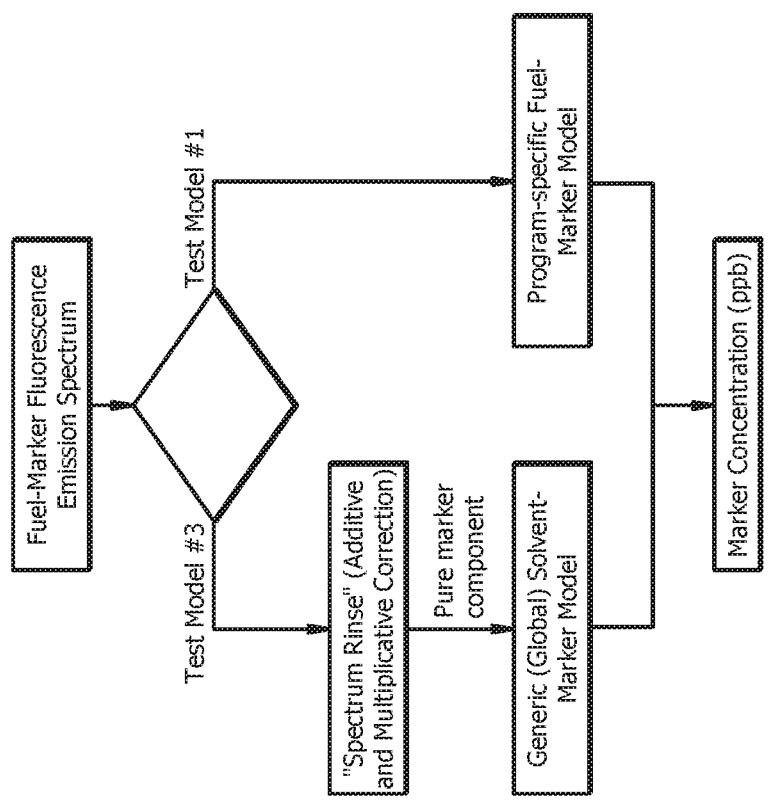
FIG. 3 displays a plot of data comparison for test models #1 and #3 of Example 2.
Figure 3:
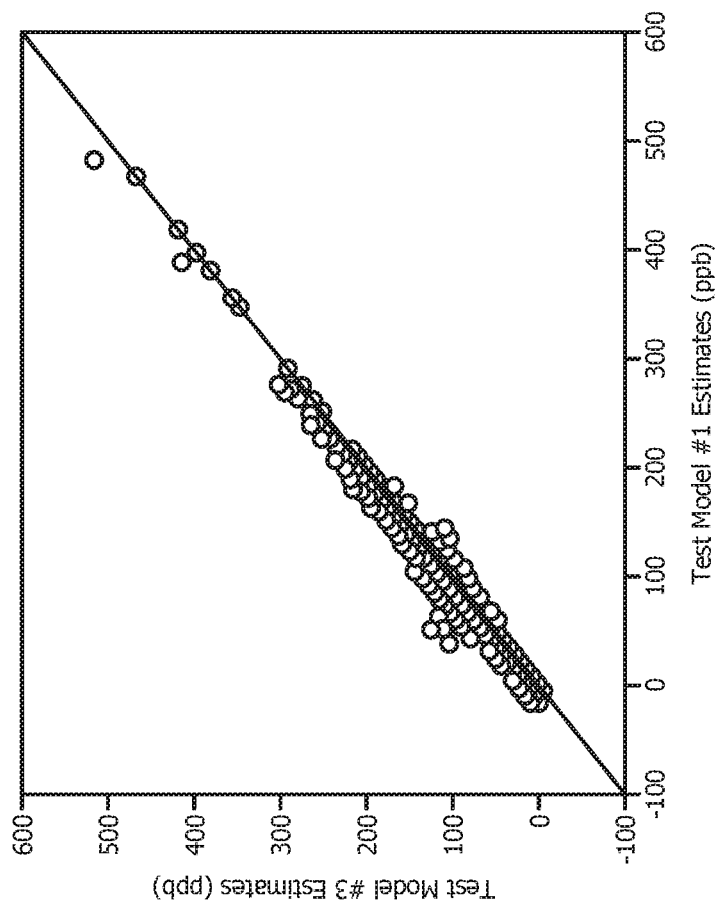

The fuel marker levels obtained from each of the 3 test models were compared to each other. Fuel marker estimates from pure component spectrum analysis (test model #3) were compared to PLS-based LSX fuel marker analysis estimates produced by using test model #1. FIG. 3 displays a comparison of the data obtained via test model #3 and the data obtained via test model #1. The statistical equivalence of the results from test model #1 and test model #3, as confirmed with the Bland-Altman test statistic, indicates that the application of the additive and multiplicative correction methods disclosed herein to fuel-marker spectra, and the application of a generic solvent/marker quantitative model to the resulting pure marker component spectrum (test model #3), perform just as well as a quantitative model that is tailored to the test samples (test model #1). The latter approach (test model #1) relies on a relatively complicated model that must account for the complexity of fuel matrix/marker interactions. The former approach (test model #3) utilizes the methods described herein (i.e., method of fuel analysis employing a projection function (W) as disclosed herein) to "shrink the model space" in a manner that allows for the use of a simple solvent-marker model for fuel marker concentration estimation that effectively becomes a global model for the marker. The Bland-Altman test statistic is described in more detail in Bland, J. M.; Altman, D. G., "Statistical method for assessing agreement between two methods of clinical measurement," The Lancet, 1986, 307-310; which is incorporated by reference herein in its entirety.

FIG. 4 displays data comparison of measured fluorescence emission spectra (left) and corrected emission spectra (right) generated via mathematical dilution according to test model #3, wherein the mathematical dilution "cleans" the data by removing additive spectral background (e.g., fluorescence signal shoulder below 700 nm in the left plot in FIG. 4) due to fuel matrix fluorescence, as well as by removing multiplicative fuel matrix effects (e.g., spectral perturbation such as solvatochromism) to resolve individual spectra for various concentrations of fuel marker in the fuel sample. The "cleaned" spectra consists primarily of the marker pure component and very little of the fuel matrix contribution and is therefore easily quantifiable with a simple solvent/marker model.

Table 2 displays a comparison of the fuel marker amounts [ppb] estimated via each of the 3 test models #1, #2, and #3.

TABLE 2

| Fuel Marker Concentration [ppb] | Test model #1 | Test model #2 | Test model #3 |
|---|---|---|---|
| 100 | 100 ± 3 ppb | 99 ± 17 ppb | 101 ± 5 ppb |
| 90 | 91 ± 2 ppb | 90 ± 16 ppb | 92 ± 5 ppb |
| 80 | 81 ± 2 ppb | 77 ± 15 ppb | 82 ± 5 ppb |
| 50-79 | 70 ± 8 ppb | 66 ± 14 ppb | 70 ± 8 ppb |

Test models #2 and #3 attempt a "real-world" application of a global or universal model, wherein the model calibration samples are significantly different from the program samples; for example Ghanaian fuels (of really poor quality) versus E.U. grade Serbian fuels (high quality fuels), which represent two extremes with respect to the continuum of fuel quality and marker/fuel matrix variation in the global supply chain. Test model #2 performs poorly because it evaluates samples from Serbia with a Ghana model without the benefit of the spectrum correction methods disclosed herein. Test model #3 is essentially a universal test model that is only viable because of the spectrum correction methods disclosed herein; as opposed to the test model #1, which is narrowly tailored to Serbian fuels. It should be noted that the "true" fuel marker concentration levels for the tested fuel samples in Table 2 are unknown, since the tested fuel samples are field samples from the fuel supply chain in the test location (Serbia). The data in Table 2 compare the same pool of test measurement distributions at specific nominal concentration levels across the 3 test models. It should be further noted that the type of data displayed in Table 2 differs from the type of data in Table 1 of Example 1. The data in Table 1 (i) are derived from spectra subjected to the correction methods disclosed herein (i.e., method of fuel analysis employing a projection function (W) as disclosed herein), as well as chemical pre-treatment; and (ii) display estimates of maker concentration levels in matrix compromised samples with known marker dosing levels, wherein the maker concentration levels are accurately reproduced (e.g., calculated).

Example 3

The measured emission spectra of from samples containing a fluorescent fuel marker were processed with three different analysis methods, as follows. Fluorescence emission spectra from test fuel samples were collected over 6 months from a location (Mexico) that is different from the one in Example 2 (Serbia). The spectra were recorded on 5 LSX2000 units for a total number of 5,230 LSX measurements for gasoline and diesel samples. The same marker from Example 2 (LSX202) was used to mark the test fuels with 100 ppb of the marker at a 100% dosing level. Test model #4 is a location specific quantitative model that is similar to test model #1 described in Example 2, i.e., the model calibration for test model #4 was developed from marked fuel samples from the particular tested location (Mexico). Test model #3 from Example 2 (i.e., method of fuel analysis employing a projection function (W) as disclosed herein, which is a generic solvent-marker model or a "global" model) was applied the test spectra from Mexico after the spectra were subjected to the spectrum correction methods described herein (e.g., constrained deconvolution for background correction). It should be noted that while the samples from which the projection matrix (W) was derived are the same in both examples (Examples 2 and 3), the version of W that was applied to the test samples from Example 3 is different from the version of W that was applied to the test samples from Example 2. This highlights the necessity of tuning W with the optimum number of factor space dimensions (a and b) to better account for the fuel-marker variation that may be unique to a target population of fuels.

Figure 5:
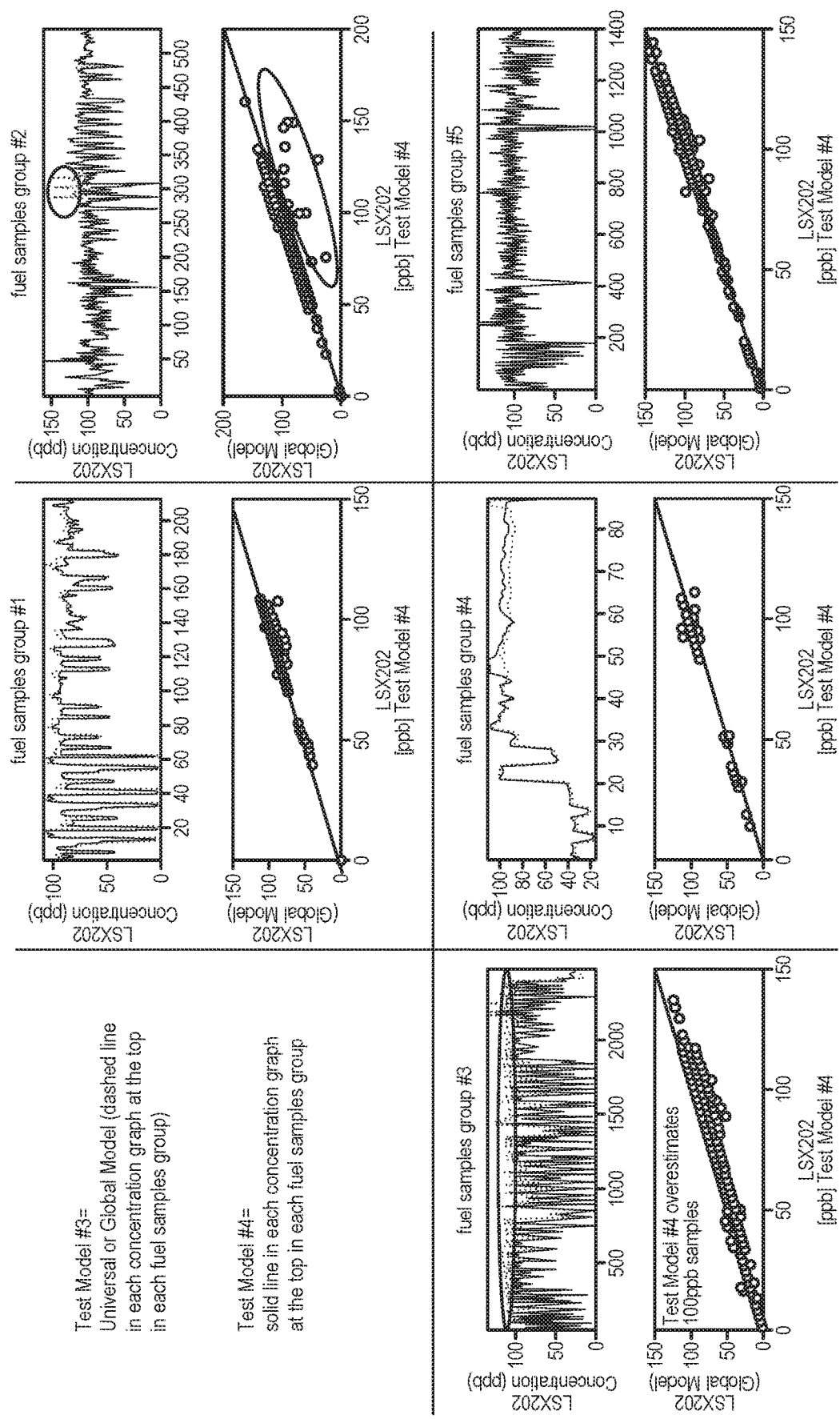
FIG. 5 displays a plot of data comparison for test models #3 and #4 of Example 3.

FIG. 5 displays a comparison between test models #3 (global) and #4 (tailored) for fuel samples acquired from each of the 5 LSX2000 units. Each of the 5 LSX2000 units tested a fuel samples group of the fuel samples groups 1-5 in FIG. 5. FIG. 5 displays a collection of 5 plot panels, wherein each panel corresponds to a fuel samples group, and wherein each panel contains a time series (upper) plot comparing the trend in tailored model estimates (test model #4) versus global model estimates (test model #3) over time; and a second (lower) plot that directly compares the concentration estimates between both models—allowing for the evaluation of linearity and bias between the two models. As was the case with Example 1, fuel marker concentration estimates from the tailored model (test model #4) were shown to be essentially equivalent to the fuel marker concentration estimates from the "global" model (test model #3), although a subset of samples (fuel samples groups #2 and #3) are overestimated by the tailored (program) model (test model #4), but accurately estimated with the global model (test model #3). Further evaluation of the fuel samples spectra indicates significant fuel fluorescence background emission that is not well accounted for with the tailored model (test model #4), but is accurately removed with the background correction method disclosed herein (i.e., constrained deconvolution for background correction).

Overall, the experimental results from Examples 2-3 indicate that the test model #3 can be used as an universal or global model, and that the accuracy of global test model #3 is good enough to replace tailored test models #1 and #4. Example 1 demonstrates how well the proposed "mathematical dilution" method mimics the regulation of a polar environment of a fuel-marker matrix using an appropriate solvent. As will be appreciated by one of skill in the art, and with the help of this disclosure, the mathematical dilution parameters (i.e., the projection function W) and quantitative model are fuel marker specific.

While the current disclosure is discussed in detail in the context of a single fuel marker used for marking the fuel, it should be appreciated by one of skill in the art that the global quantitative test model and the projection function can be expanded to include more than a single fluorescence marker.

Example 4

The effect of temperature on fluorescence spectra was further investigated. Two Diesel fuel samples were dosed with a proprietary quantum photonic marker (LSX202) at 100 ppb. The emission spectra from the fuel-marker mixtures were recorded at temperatures ranging from 5° C. to 45° C. with LSX3000 fuel analyzers that each included a short-wave near infrared spectrometer from Ocean Optics with a charge-coupled device (CCD) detector. An average of 10 emission spectra were acquired from each sample at each temperature with a boxcar window width of 3.

Figure 7A:
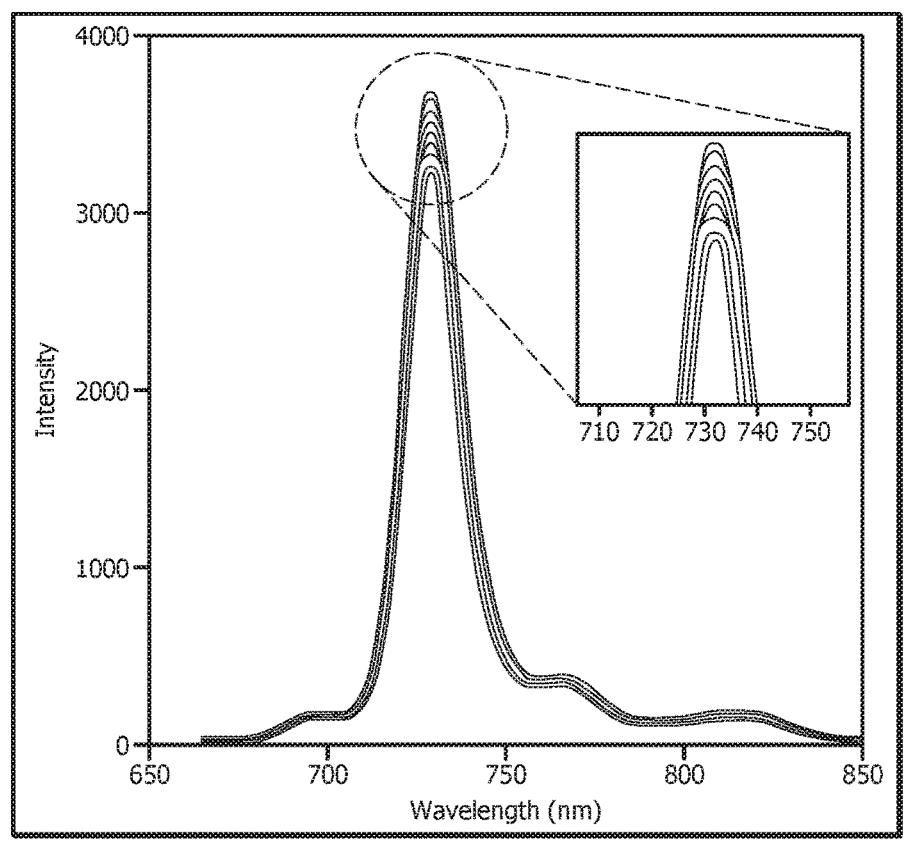
FIG. 7A displays spectra from a fluorescence spectrometer analyzer where the detector is temperature-controlled, but sample (e.g., sample holder or chamber) is not temperature-controlled.
Figure 7B:
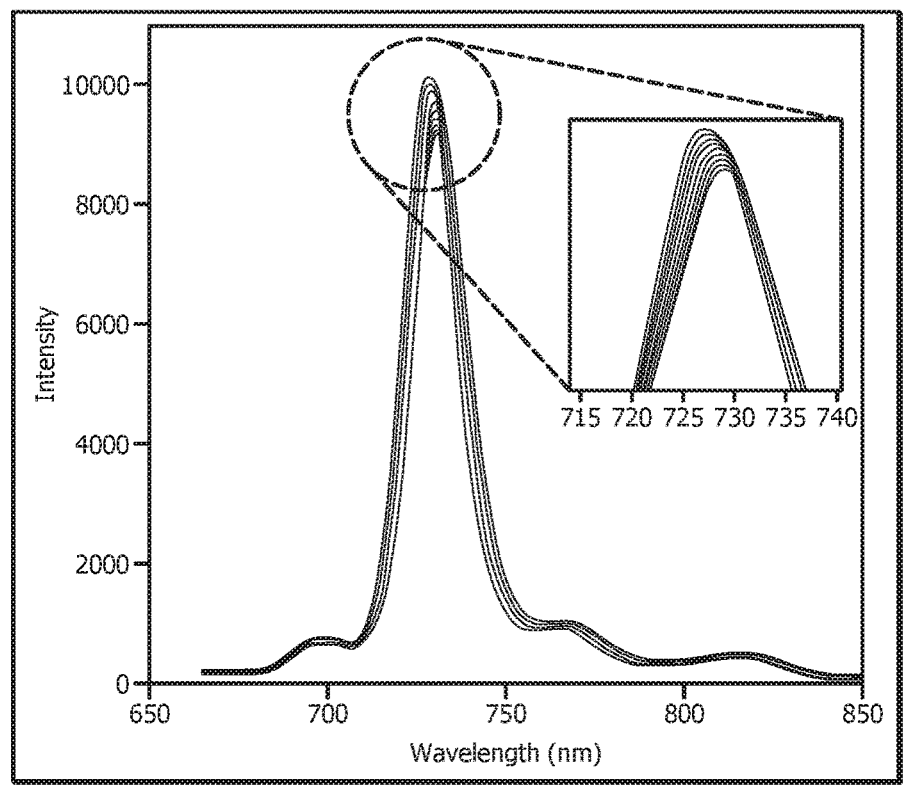
FIG. 7B displays spectra from a fluorescence spectrometer analyzer where neither the detector nor the sample are temperature-controlled.

As will be appreciated by one of skill in the art, and with the help of this disclosure, and without wishing to be limited by theory, the intensity of fluorescence emission (e.g., signal intensity) is affected by temperature, wherein there is an inverse relationship between sample temperature and fluorescence emission intensity. Further, and as will be appreciated by one of skill in the art, and with the help of this disclosure, the impact of temperature on fluorescence measurements for spectrometers using CCD array detectors is fairly complex. In the case of CCD array detectors, both the fluorescence intensity and spectrum shape is modified with temperature. The latter property (spectrum shape) is distorted by the nonlinear CCD pixel (e.g., CCD element) response to temperature. The effect of temperature on sample measurements where the neither the sample nor the detector are temperature-controlled is shown in FIGS. 7A and 7B. FIG. 7A displays signal intensity variation with temperature. FIG. 7B displays signal intensity variation as well as bandwidth change (e.g., spectrum shape distortion) with temperature. The intensity changes of sample fluorescence were affected by temperature was as expected from fluorescence behavior of marker with temperature. The shape of the spectra was intact since the detector was temperature controlled (FIG. 7A). The spectrum shape was distorted in FIG. 7B due to the CCD element response to temperature, since the detector was not temperature controlled. The shape changes would give variable results of the marker concentrations, thereby indicating the importance of correcting the effect of temperature for these spectra.

Example 5

The effect of temperature on fluorescence spectra was further investigated. Two Diesel fuel samples were dosed with a proprietary quantum photonic marker (LSX202) at 100 ppb. The emission spectra from the fuel-marker mixtures were recorded at temperatures ranging from 5° C. to 45° C. with LSX3000 fuel analyzers that each included a short-wave near infrared spectrometer from Ocean Optics with a CCD detector. An average of 10 emission spectra were acquired from each sample at each temperature with a boxcar window width of 3.

Figure 8:
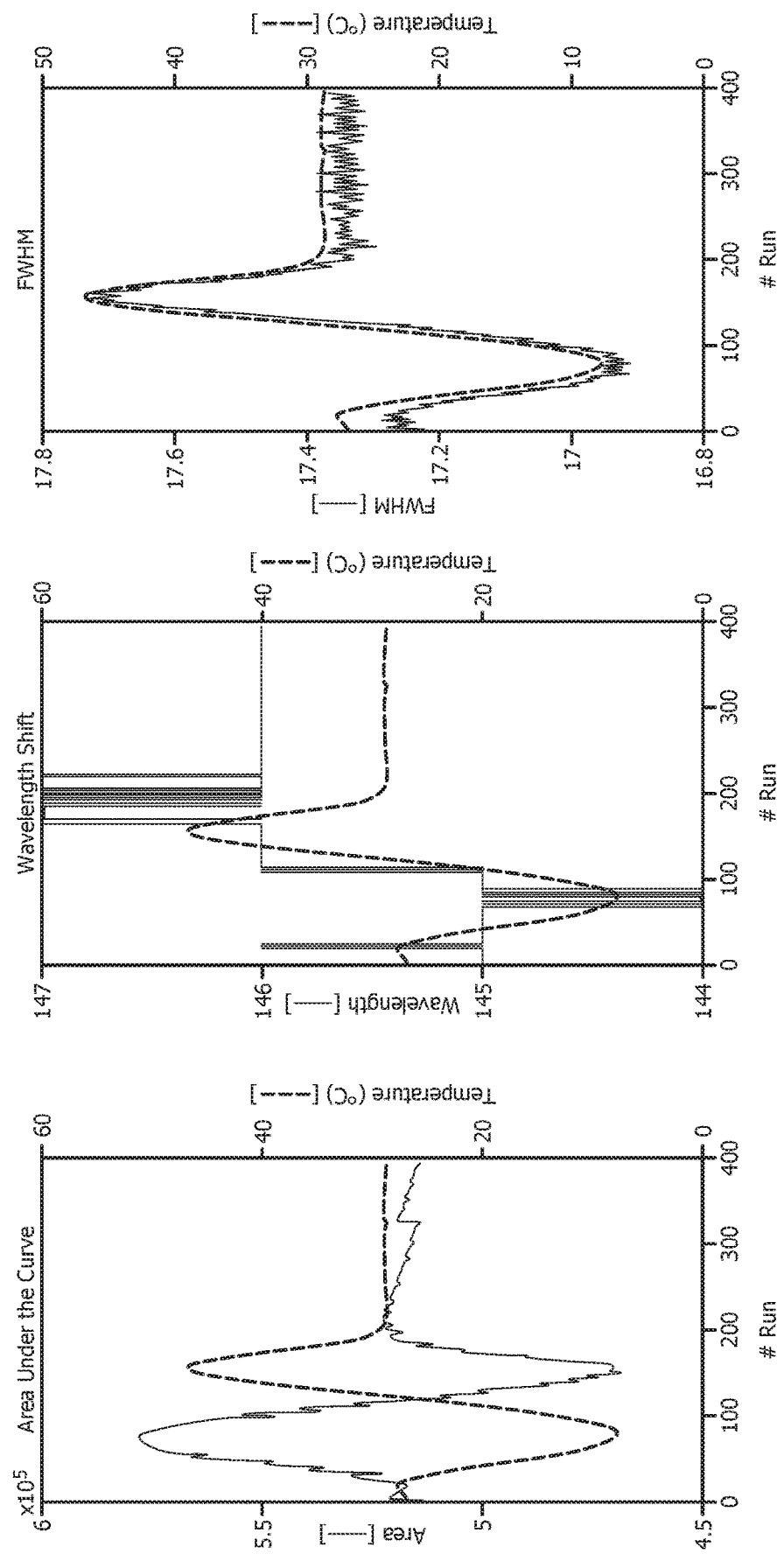
FIG. 8 displays area under the curve, peak wavelength, and full width half maximum (FWHM) derived from spectra that were generated from a marked diesel sample at temperatures ranging from 5° C. to 45° C.

Specifically, the effect of temperature (5° C. to 45° C.) was investigated for changes in integrated spectrum area (e.g., signal intensity), peak wavelength position, and full width at half maximum (FWHM) were all evaluated with a marked diesel sample, and the results are displayed in FIG. 8. For the data in FIG. 8, the spectra from a marked diesel sample were recorded on a fluorescence spectrometer where neither the sample nor the detector were temperature-controlled. FIG. 8 shows the changes in shape of the fluorescence spectra as a function of temperature. The area under the curve (spectrum) varies in a manner that is inversely proportional to the temperature variation. The wavelength shift and FWHM display about the same change pattern as the temperature variation, which is due to changes in the CCD elements with temperature. The lack of temperature control for detector results in spectrum shape distortions and would further result in inaccurate marker quantification estimates.

Example 6

The effect of temperature on fluorescence spectra was further investigated. Two Diesel fuel samples were dosed with a proprietary quantum photonic marker (LSX202) at 100 ppb. The emission spectra from the fuel-marker mixtures were recorded at temperatures ranging from 5° C. to 45° C. with LSX3000 fuel analyzers that each included a short-wave near infrared spectrometer from Ocean Optics with a CCD detector. An average of 10 emission spectra were acquired from each sample at each temperature with a boxcar window width of 3.

Figure 9A:
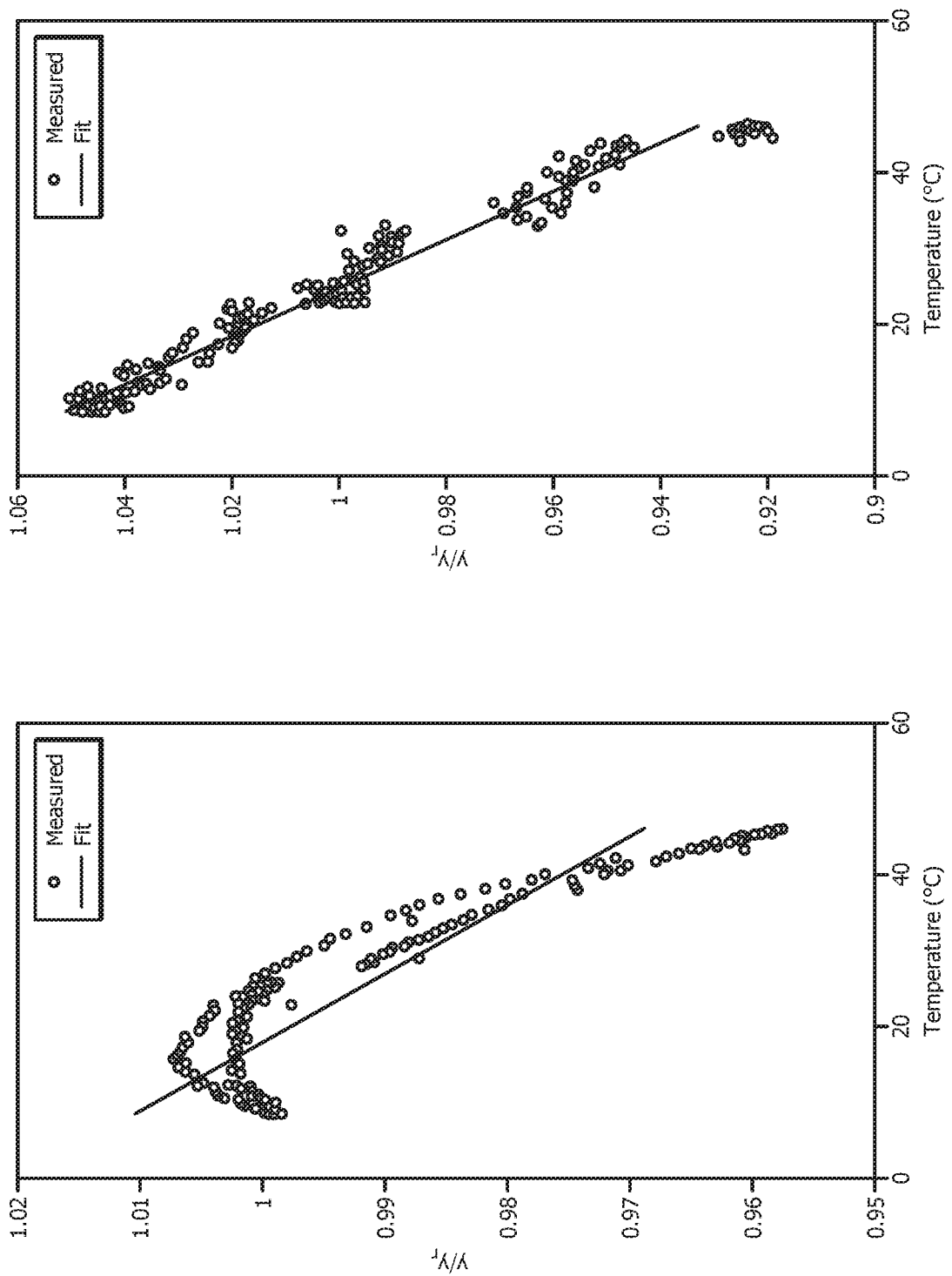
FIG. 9A displays a plot of normalized concentration ($y/y_r$) versus temperature for diesel sample #1 on analyzer #1 (i.e., fluorescence spectrometer #1)
Figure 9B:
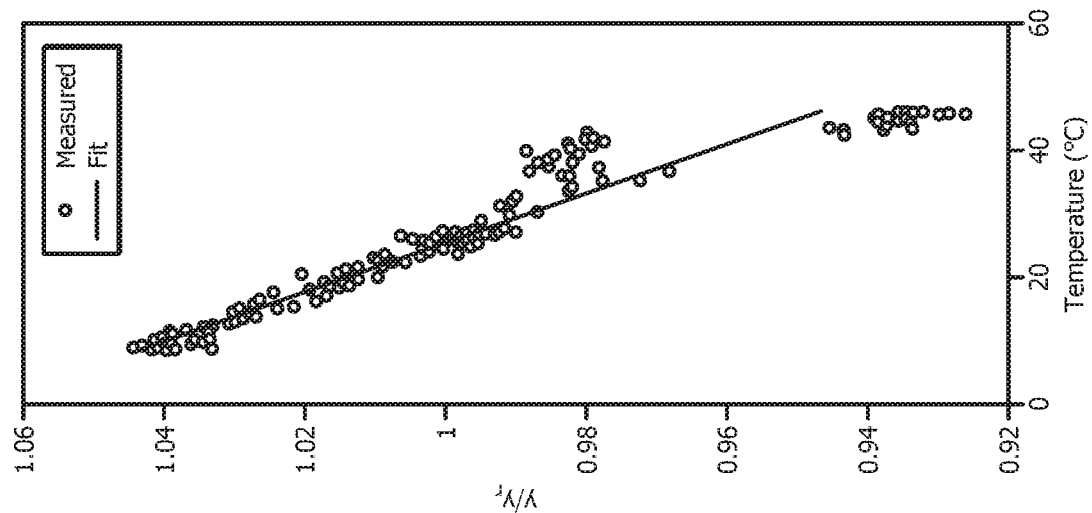
FIG. 9B displays a plot of normalized concentration ($y/y_r$) versus temperature for diesel sample #2 on analyzer #2 (i.e., fluorescence spectrometer #2)
Figure 9B:
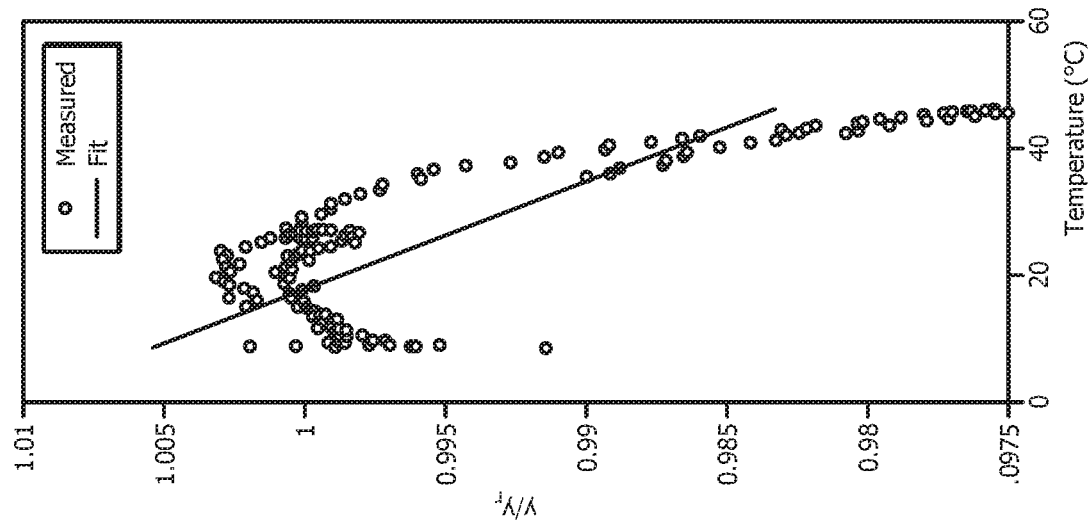
Figure 10A:
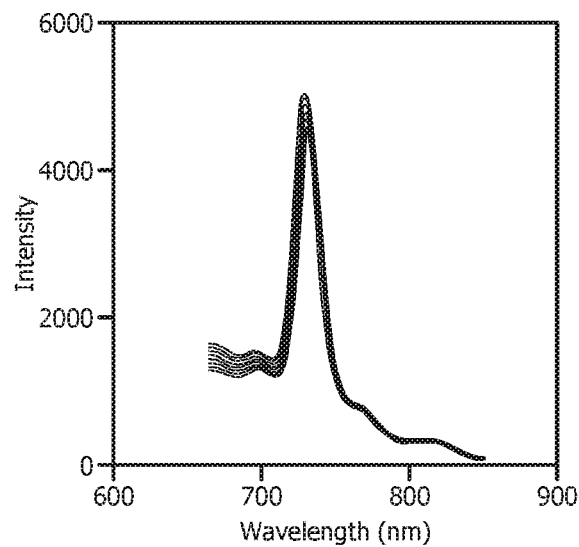
FIGS. 10A-10D display fluorescence emission spectra of a fuel marker in diesel over a temperature range from 5° C.-45° C. (10A); after peak wavelength shift and baseline correction (10B); $y/y_r$ versus temperature plot post spectrum transformation (e.g., projection function decoupling) (10C); and $y/y_r$ versus temperature plot post temperature correction (10D)
Figure 10B:
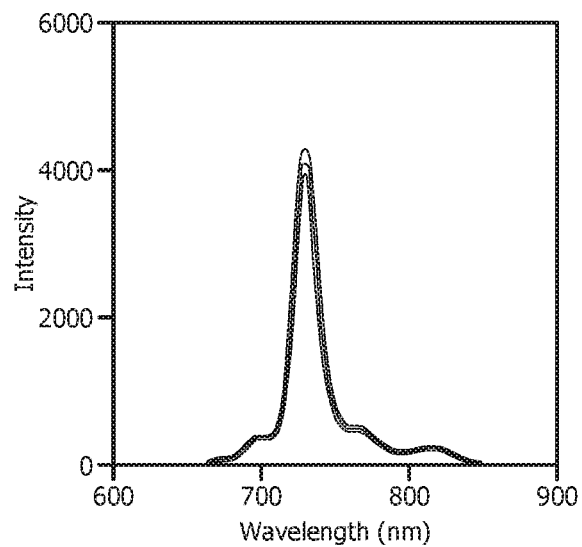
Figure 10C:
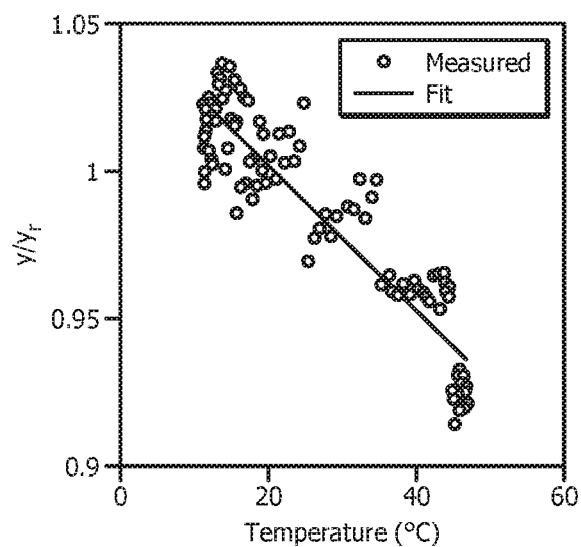
Figure 10D:
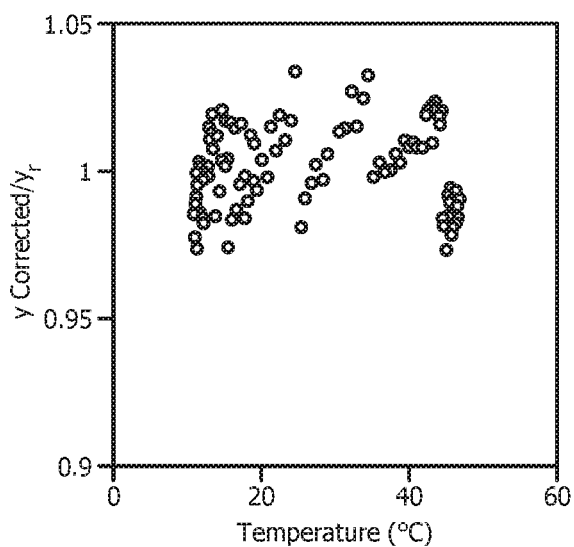

FIGS. 9A and 9B demonstrate the application of temperature correction to the signal intensity over a temperature range from 5° C. to 45° C. at a fixed fuel marker concentration for two Diesel samples measured with two analyzers or spectrometers (#1 and #2). The fitting parameters ($y/y_r$) are generalizable across fuel types (e.g., Diesel, gasoline, solvent) and even across different spectrometers or analyzers. Therefore, using the parameters derived from solutions of fuel marker in solvent obtained for spectra from one spectrometer can effectively adjust the concentration of the fuel marker in fuel samples for spectra from other spectrometers for temperature, thereby producing results that are significantly more precise compared to spectra that are not corrected for temperature.

Unlike the plots on the right in FIGS. 9A and 9B, the plots on the left in FIGS. 9A and 9B display $y/y_r$ versus temperature trends derived from spectra that have not been subjected to the background correction/peak correction/matrix normalization method based on projection function decoupling as disclosed herein. The plots on the left in FIGS. 9A and 9B display temperature trends that are nonlinear because they combine intensity, bandwidth and peak wavelength variations, which also vary from sample to sample. By contrast, the plots on the right in FIGS. 9A and 9B display linear temperature trends that are relatively consistent across samples and spectrometers.

FIGS. 10A-10D demonstrate temperature compensation of Diesel sample emission measurements from spectrometer #1. The correction ($y/y_r$) improves the relative standard deviation of measurements from 5° C. to 45° C. from 5.1% to 1.43% (a 71% improvement in measurement precision). This improvement would result in consistent quantification estimates across the temperature range.

Example 7

The effect of temperature on fluorescence spectra was further investigated. Diesel fuel samples were dosed with a proprietary quantum photonic marker (LSX202) at 100 ppb. The emission spectra from the fuel-marker mixtures were recorded with an LSX3000 fuel analyzer that included a short-wave near infrared spectrometer from Ocean Optics with a CCD detector. An average of 10 emission spectra were acquired from each sample at each temperature with a boxcar window width of 3.

In order to demonstrate how the method of spectra correction as disclosed herein corrects for the effect of temperature on fluorescence emission measurements, a series of measurements were made with a spectrometer whose temperature was maintained at about 26° C. The spectrometer was fitted with an IR thermocouple for logging sample temperature.

Figure 11:
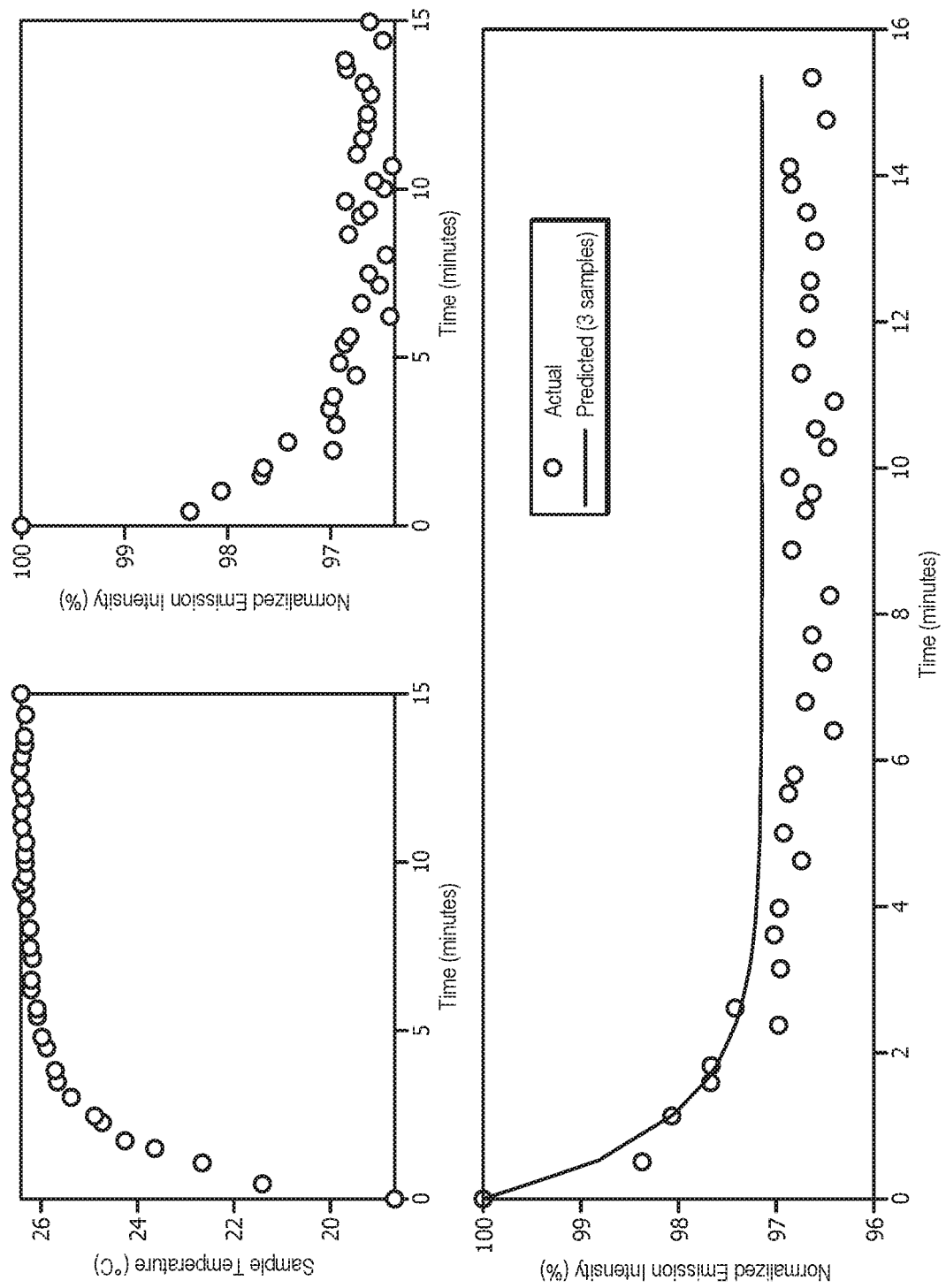
FIG. 11 displays the prediction of the steady-state fluorescence emission value from a sample that is cooled to 19° C. with 3 emission and temperature measurements.

In a first experiment, a fuel sample that was dosed (e.g., marked) with a fluorescent marker was cooled to 19° C. before placing it in the spectrometer. The sample temperature, as well as the normalized emission intensity were continuously tracked for about 15 minutes, by which time both parameters (i.e., signal intensity and sample temperature) were at steady-state, and the data are displayed in FIG. 11. By applying the first three measurements in each time series (which translates into a minute's worth of emission measurements), to the equations (6)-(9), it was possible to predict the steady-state value of the normalized intensity (C in equation (9)). It should be noted that the predicted decay curve (i.e., line curve) in FIG. 11 matches well with the actual measurements (i.e., hollow circles curve). The method of spectra correction as disclosed herein was able to cut short the measurements by 3 minutes (the actual steady-state was achieved after 4 minutes), and was also able to accurately predict an about 3% drop in fluorescence relative to the initial fluorescence emission measurement. In FIG. 11, the sample emission intensity decayed with time, while the sample temperature grew with time as it synced up to the spectrometer (reference) temperature. A steady-state intensity that was 3% less than the initial emission intensity was predicted from only 3 measurements versus a true steady-state value that was about 3.3% less than the initial intensity.

Figure 12:
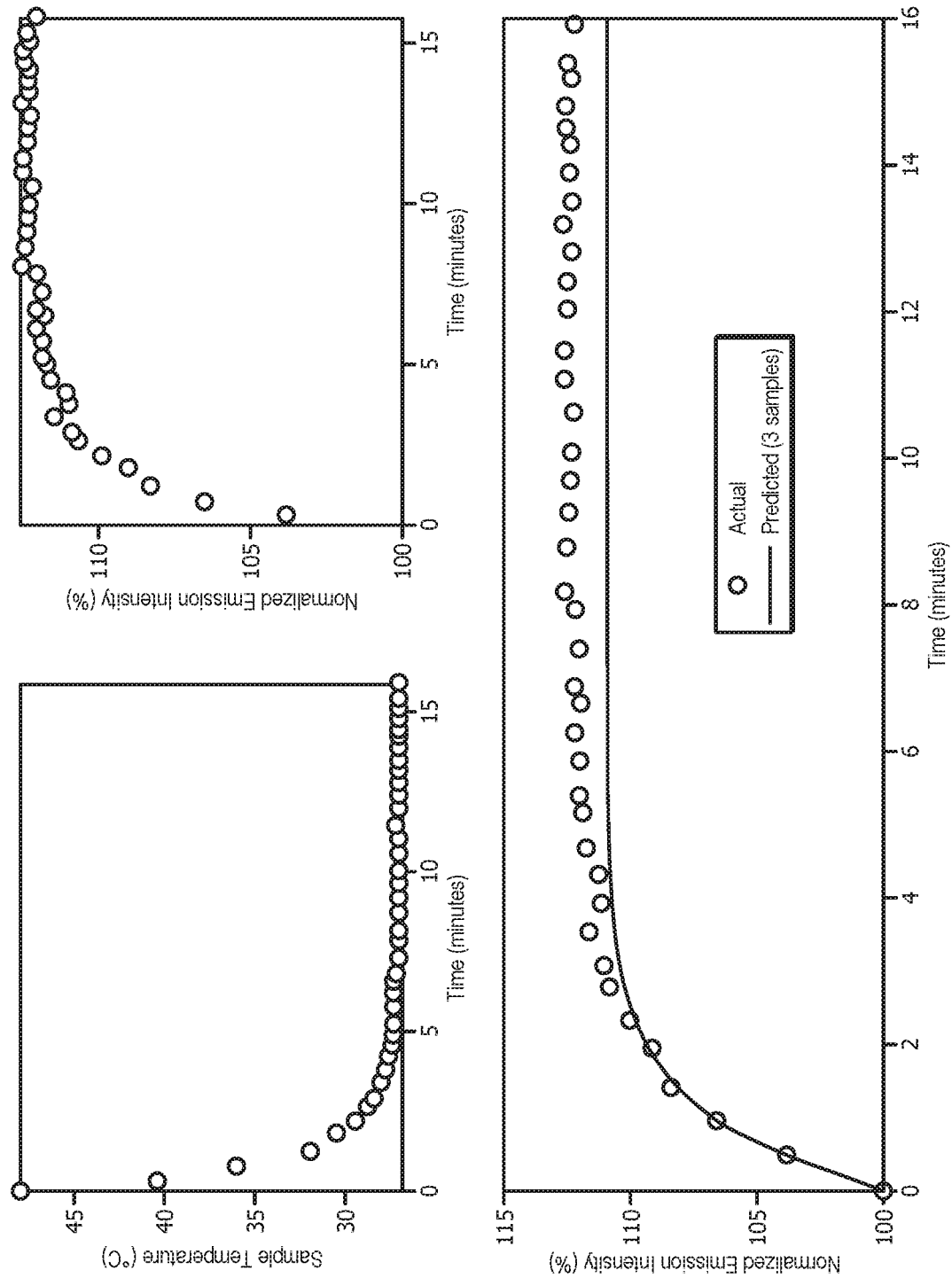
FIG. 12 displays the prediction of the steady-state fluorescence emission value from a sample that is heated to 50° C. with 3 emission and temperature measurements.

In a second experiment, the sample was heated to 50° C. in which case the emission was expected to rise as the sample temperature equilibrated with that of the spectrometer, and the data are displayed in FIG. 12. Again, and similarly to the data in FIG. 11, by using the first 3 measurements from each time series, the method of spectra correction as disclosed herein predicted a 10% rise in fluorescence emission versus a steady-state value of about 11%. In FIG. 12, the sample emission intensity grew with time, while the sample temperature decayed with time as it synced up to the spectrometer (reference) temperature. A steady-state intensity that was 10% more than the initial emission intensity was predicted versus a true steady-state value that was about 11% more than the initial intensity.

The method of spectra correction as disclosed herein can allow for a quick adjustment of the sample fluorescence intensity using steady-state estimates that are derived from 3 repeat measurements. All data correction methods disclosed herein can provide for facilitating temperature adjustments that are aimed at producing consistently precise measurements across a range of temperatures.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37

C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

Aspects Group A

A first aspect, which is a method of fuel analysis comprising (a) subjecting a fuel sample to fluorescence spectroscopy to generate a measured emission spectrum, wherein the fuel comprises a fuel marker and a fuel matrix, and wherein the measured emission spectrum comprises a first spectral component corresponding to type and amount of fuel marker in the fuel sample, a second spectral component corresponding to a spectral perturbation, and a third spectral component corresponding to fuel matrix fluorescence; (b) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; (c) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of at least a portion of the second spectral component to yield the corrected emission spectrum; and (d) determining the amount of fuel marker in the fuel sample from the corrected emission spectrum.

A second aspect, which is the method of the first aspect, wherein the step (b) of deconvoluting the measured emission spectrum comprises removal of additive fuel matrix fluorescence baseline via a three-step process, wherein the three-step process comprises (i) an iterative fit of the measured emission spectrum to a reference spectrum to yield a residual spectrum; (ii) applying shape-preserving piecewise cubic hermite interpolating polynomial (pchip) to the residual spectrum to yield a reconstituted residual spectrum; and (iii) subtracting the reconstituted residual spectrum from the measured emission spectrum to yield the deconvoluted measured emission spectrum.

A third aspect, which is the method of any one of the first and the second aspects, wherein the step (c) of decoupling the deconvoluted measured emission spectrum comprises the removal of multiplicative fuel matrix perturbation via the projection function.

A fourth aspect, which is the method of any one of the first through the third aspects, wherein the spectral perturbation comprises fuel matrix effects that induce spectral inconsistencies in similarly marked fuel samples.

A fifth aspect, which is the method of any one of the first through the fourth aspects, wherein the spectral perturbation comprises solvatochromism.

A sixth aspect, which is the method of any one of the first through the fifth aspects, wherein the projection function is derived by comparing an emission fluorescence spectrum of a marked fuel sample comprising a known amount of fuel marker and fuel with an emission fluorescence spectrum of one or more marked solvent solutions comprising a known amount of fuel marker and a solvent.

A seventh aspect, which is the method of the sixth aspect, wherein comparing an emission fluorescence spectrum of a marked fuel sample with an emission fluorescence spectrum of one or more marked solvent solutions further comprises principal components regression analysis.

An eighth aspect, which is the method of any one of the first through the fourth aspects, wherein the projection function is derived by comparing an emission fluorescence spectrum of a marked fuel sample comprising a spectral perturbation with an emission fluorescence spectrum of the same marked fuel sample that has been chemically pre-treated to remove at least a portion of the spectral perturbation.

A ninth aspect, which is the method of the eighth aspect, wherein comparing an emission fluorescence spectrum of a marked fuel sample with an emission fluorescence spectrum of the chemically pre-treated marked fuel sample comprises determining a least square estimator of a multiple linear regression (MLR) model that fits the emission fluorescence spectrum of the marked fuel sample to the emission fluorescence spectrum of the chemically pre-treated marked fuel sample.

A tenth aspect, which is the method of any one of the eighth and the ninth aspects, wherein the subspace devoid of the second spectral component is based on the emission fluorescence spectrum of the chemically pre-treated marked fuel sample.

An eleventh aspect, which is the method of any one of the eighth through the tenth aspects, wherein the subspace devoid of the second spectral component is derived from the emission fluorescence spectrum of the chemically pre-treated marked fuel sample via matrix decomposition analysis using singular value decomposition (SVD) or principal components analysis (PCA).

A twelfth aspect, which is the method of any one of the first through the eleventh aspects, wherein the step (d) of determining the amount of fuel marker in the fuel sample comprises a least square fitting of the corrected emission spectrum to an emission fluorescence spectrum of one or more marked solvent solutions comprising a known amount of fuel marker and a solvent.

A thirteenth aspect, which is the method of any one of the first through the eleventh aspects, wherein the step (d) of determining the amount of fuel marker in the fuel sample comprises partial least squares (PLS) regression.

A fourteenth aspect, which is the method of any one of the first through the thirteenth aspects, wherein the fuel comprises gasoline, diesel, jet fuel, kerosene, liquefied petroleum gas, non-petroleum derived fuels, alcohol fuels, ethanol, methanol, propanol, butanol, biodiesel, maritime fuels, or combinations thereof.

A fifteenth aspect, which is the method of any one of the first through the fourteenth aspects, wherein the fuel marker is present in the fuel sample in an amount of from about 0.1 ppb to about 1,000 ppb, based on the total weight of the fuel sample.

A sixteenth aspect, which is the method of any one of the first through the fifteenth aspects further comprising determining adulteration of the fuel by comparing the amount of fuel marker in the fuel sample to a target amount of fuel marker, wherein the target amount of fuel marker is a known amount of fuel marker used to mark the fuel by a fuel supplier.

A seventeenth aspect, which is a method of fuel analysis comprising (a) acquiring a fuel sample; (b) subjecting the fuel sample to fluorescence spectroscopy to generate a measured emission spectrum, wherein the fuel comprises a fuel marker and a fuel matrix, wherein the measured emission spectrum comprises a first spectral component corresponding to type and amount of fuel marker in the fuel sample, a second spectral component corresponding to a spectral perturbation, and a third spectral component corresponding to fuel matrix fluorescence, and wherein the spectral perturbation comprises fuel marker solvatochromism; (c) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; (d) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum; (e) determining the amount of fuel marker in the fuel sample from the corrected emission spectrum; and (f) determining adulteration of the fuel by comparing the amount of fuel marker in the fuel sample to a target amount of fuel marker, wherein the target amount of fuel marker is a known amount of fuel marker used to mark the fuel by a fuel supplier.

An eighteenth aspect, which is the method of the seventeenth aspect, wherein the step (a) of acquiring a fuel sample further comprises determining the presence of the fuel marker in the fuel sample.

A nineteenth aspect, which is the method of any one of the seventeenth and the eighteenth aspects, wherein the fuel sample is a liquid sample.

A twentieth aspect, which is the method of any one of the seventeenth through the nineteenth aspects, wherein the projection function is fuel marker specific.

Aspects Group B

A twenty-first aspect, which is a method of fuel analysis comprising (a) obtaining a measured emission spectrum, via fluorescence spectroscopy, from a fuel sample by utilizing a fluorescence spectrometer; wherein the fluorescence spectrometer comprises a detector and a temperature-controlled excitation source; wherein the fuel sample and the detector are not temperature-controlled; wherein the fuel comprises a fuel marker and a fuel matrix; wherein the measured emission spectrum comprises a first spectral component corresponding to type and amount of fuel marker in the fuel sample, a second spectral component corresponding to a spectral perturbation, and a third spectral component corresponding to fuel matrix fluorescence; and wherein the spectral perturbation comprises a temperature perturbation and/or a fuel matrix perturbation; (b) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; (c) decoupling the deconvoluted measured emission spectrum to yield a corrected emission spectrum via a fuel matrix projection function, wherein the corrected emission spectrum comprises the first spectral component, and wherein the fuel matrix projection function orthogonally projects the deconvoluted measured emission spectrum onto a subspace devoid of at least a portion of the second spectral component to yield the corrected emission spectrum; and (d) determining the amount of fuel marker in the fuel sample from the corrected emission spectrum.

A twenty-second aspect, which is the method of the twenty-first aspect, wherein the step (b) of deconvoluting the measured emission spectrum comprises removal of additive fuel matrix fluorescence baseline via a three-step process, wherein the three-step process comprises (i) an iterative fit of the measured emission spectrum to a reference spectrum to yield a residual spectrum; (ii) applying shape-preserving piecewise cubic hermite interpolating polynomial (pchip) to the residual spectrum to yield a reconstituted residual spectrum; and (iii) subtracting the reconstituted residual spectrum from the measured emission spectrum to yield the deconvoluted measured emission spectrum.

A twenty-third aspect, which is the method of any one of the twenty-first and the twenty-second aspects, wherein the fuel matrix projection function is derived by comparing an emission fluorescence spectrum of a marked fuel sample comprising a known amount of fuel marker and fuel with an emission fluorescence spectrum of one or more marked solvent solutions comprising a known amount of fuel marker and a solvent; and wherein comparing an emission fluorescence spectrum of a marked fuel sample with an emission fluorescence spectrum of one or more marked solvent solutions further comprises principal components regression analysis.

A twenty-fourth aspect, which is the method of any one of the twenty-first through the twenty-third aspects further comprising (i) decoupling the deconvoluted measured emission spectrum to yield a temperature corrected emission spectrum via a temperature projection function, wherein the temperature corrected emission spectrum comprises the first spectral component and a portion of the second spectral component, and wherein the temperature projection function orthogonally projects the deconvoluted measured emission spectrum onto a subspace devoid of the temperature perturbation to yield the temperature corrected emission spectrum; and (ii) decoupling the temperature corrected emission spectrum to yield a corrected emission spectrum via a fuel matrix projection function, wherein the corrected emission spectrum comprises the first spectral component, and wherein the fuel matrix projection function orthogonally projects the temperature corrected emission spectrum onto a subspace devoid of the fuel matrix perturbation to yield the corrected emission spectrum.

A twenty-fifth aspect, which is the method of the twenty-fourth aspect, wherein the temperature projection function is derived by comparing emission fluorescence spectra of a marked fuel sample comprising a known amount of fuel marker; wherein the emission fluorescence spectra are recorded at two or more different temperatures; and wherein comparing emission fluorescence spectra comprises principal components regression analysis.

A twenty-sixth aspect, which is the method of any one of the twenty-first through the twenty-fifth aspects, wherein the subspace devoid of at least a portion of the second spectral component is devoid of the fuel matrix perturbation and of the temperature perturbation.

A twenty-seventh aspect, which is the method of any one of the twenty-first through the twenty-sixth aspects, wherein the fluorescence spectrometer is a portable fluorescence spectrometer.

A twenty-eighth aspect, which is the method of any one of the twenty-first through the twenty-third aspects, wherein the step (c) of decoupling the deconvoluted measured emission spectrum comprises the removal of multiplicative fuel matrix perturbation via the fuel matrix projection function.

A twenty-ninth aspect, which is the method of the twenty-eighth aspect, wherein the step (c) of decoupling the deconvoluted measured emission spectrum further comprises the removal of the temperature perturbation via the fuel matrix projection function.

A thirtieth aspect, which is the method of any one of the twenty-first through the twenty-ninth aspects, wherein the fuel matrix perturbation comprises fuel matrix effects that induce spectral inconsistencies in similarly marked fuel samples; and wherein the temperature perturbation comprises temperature effects that induce wavelength shift and/or bandwidth changes.

An thirty-first aspect, which is the method of any one of the twenty-first through the thirtieth aspects further comprising correcting the measured emission spectrum and/or the corrected emission spectrum for wavelength by matching peak wavelength with a reference fuel marker fluorescence emission wavelength.

A thirty-second aspect, which is the method of any one of the twenty-first through the thirty-first aspects, wherein the step (d) of determining the amount of fuel marker in the fuel sample comprises (1) determining an apparent amount of fuel marker in the fuel sample at the fuel sample temperature; and (2) applying a correction factor to the apparent amount of fuel marker in the fuel sample at the fuel sample temperature to yield a corrected amount of fuel marker in the fuel sample at a reference temperature.

A thirty-third aspect, which is the method of the thirty-second aspect, wherein the correction factor correlates apparent known amounts of fuel marker in solvent with reference known amounts of fuel marker in solvent across a temperature range.

A thirty-fourth aspect, which is the method of the thirty-third aspect, wherein the temperature range is from about −10° C. to about 60° C.

A thirty-fifth aspect, which is the method of the thirty-second aspect, wherein the correction factor corrects for fluorescence emission intensity variations induced by temperature variations.

A thirty-sixth aspect, which is the method of the thirty-second aspect further comprising determining adulteration of the fuel by comparing the corrected amount of fuel marker in the fuel sample to a target amount of fuel marker, wherein the target amount of fuel marker is a known amount of fuel marker used to mark the fuel by a fuel supplier.

A thirty-seventh aspect, which is the method of any one of the twenty-first through the thirty-sixth aspect, wherein the fuel comprises gasoline, diesel, jet fuel, kerosene, liquefied petroleum gas, non-petroleum derived fuels, alcohol fuels, ethanol, methanol, propanol, butanol, biodiesel, maritime fuels, or combinations thereof; and wherein the fuel marker is present in the fuel sample in an amount of from about 0.1 ppb to about 1,000 ppb, based on the total weight of the fuel sample.

An thirty-eighth aspect, which a method of fuel analysis comprising (a) acquiring a fuel sample; (b) obtaining a measured emission spectrum, via fluorescence spectroscopy, from a fuel sample by utilizing a portable fluorescence spectrometer; wherein the fluorescence spectrometer comprises a detector and a temperature-controlled excitation source; wherein the fuel sample and the detector are not temperature-controlled; wherein the fuel comprises a fuel marker and a fuel matrix; wherein the measured emission spectrum comprises a first spectral component corresponding to type and amount of fuel marker in the fuel sample, a second spectral component corresponding to a spectral perturbation, and a third spectral component corresponding to fuel matrix fluorescence; wherein the spectral perturbation comprises a temperature perturbation and a fuel matrix perturbation; wherein the fuel matrix perturbation comprises fuel marker solvatochromism; and wherein the temperature perturbation comprises wavelength shift and/or bandwidth changes; (c) correcting the measured emission spectrum for wavelength to yield a wavelength-corrected measured emission spectrum by matching peak wavelength with a reference fuel marker fluorescence emission wavelength; (d) deconvoluting the wavelength-corrected measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component; (e) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum; (f) determining an apparent amount of fuel marker in the fuel sample at the fuel sample temperature from the corrected emission spectrum; (g) applying a correction factor to the apparent amount of fuel marker in the fuel sample at the fuel sample temperature to yield a corrected amount of fuel marker in the fuel sample at a reference temperature; and (h) determining adulteration of the fuel by comparing the corrected amount of fuel marker in the fuel sample to a target amount of fuel marker, wherein the target amount of fuel marker is a known amount of fuel marker used to mark the fuel by a fuel supplier.

A thirty-ninth aspect, which is the method of the thirty-eighth aspect, wherein the step (a) of acquiring a fuel sample further comprises determining the presence of the fuel marker in the fuel sample.

A fortieth aspect, which is the method of any one of the thirty-eighth and the thirty-ninth aspects, wherein (1) the precision of the corrected amount of fuel marker is increased by equal to or greater than about 50% when compared to the precision of the amount of fuel marker determined by an otherwise similar method of fuel analysis that does not employ a projection function and/or a correction factor; and/or (2) the accuracy of the corrected amount of fuel marker is increased by equal to or greater than about 5% when compared to the accuracy of the amount of fuel marker determined by an otherwise similar method of fuel analysis that does not employ a projection function and/or a correction factor.

Aspects Group C

A forty-first aspect, which is a method of fuel analysis comprising (a) placing a fuel sample in a fluorescence spectrometer; wherein the fluorescence spectrometer comprises a temperature-controlled detector and a temperature-controlled excitation source; wherein the temperature-controlled detector and the temperature-controlled excitation source are characterized by a spectrometer temperature; wherein the fuel sample is not temperature-controlled; wherein the fuel sample is characterized by a sample temperature, and wherein the sample temperature is different from the spectrometer temperature; wherein the fuel comprises a fuel marker; wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively; (b) acquiring, via the fluorescence spectrometer, two or more measured emission spectra of the fuel sample during the first half of the equilibration time period; (c) deriving a signal intensity corresponding to the fuel marker from each measured emission spectrum; (d) generating a signal intensity variation over time curve and a sample temperature variation over time curve, wherein the signal intensity decreases with the sample temperature increasing over time or increases with the sample temperature decreasing over time; and wherein the signal intensity decrease or increase follows an exponential decay or growth curve over time, respectively; (e) estimating a signal intensity corresponding to the fuel marker at the end of the equilibration time period; and (f) determining the amount of fuel marker in the fuel sample from the estimated signal intensity corresponding to the fuel marker at the end of the equilibration time period.

A forty-second aspect, which is the method of the forty-first aspect, wherein the amount of fuel marker in the fuel sample is determined over a time period that is less than about 50% of the equilibration time period.

A forty-third aspect, which is the method of any one of the forty-first and the forty-second aspects, wherein the amount of fuel marker in the fuel sample is determined over a time period that is less than about 25% of the equilibration time period.

A forty-fourth aspect, which is the method of any one of the forty-first through the forty-third aspects, wherein the temperature exponential growth or decay curve over time is characterized by a temperature growth or decay constant, respectively; wherein the signal intensity exponential decay or growth curve over time is characterized by a signal intensity decay or growth constant, respectively; wherein the temperature growth constant is equivalent to the signal intensity decay constant; wherein the temperature growth constant is the inverse function of the signal intensity decay constant; wherein the signal intensity growth constant is equivalent to the temperature decay constant; and wherein the signal intensity growth constant is the inverse function of the temperature decay constant.

A forty-fifth aspect, which is the method of any one of the forty-first through the forty-fourth aspects, wherein the temperature of the sample is monitored with an infrared (IR) thermocouple.

A forty-sixth aspect, which is the method of any one of the forty-first through the forty-fifth aspects, wherein the step (e) of estimating a signal intensity corresponding to the fuel marker at the equilibration time comprises least squares minimization.

A forty-seventh aspect, which is the method of any one of the forty-first through the forty-sixth aspects, wherein each measured emission spectrum comprises a first spectral component corresponding to type and amount of fuel marker in the fuel sample, a second spectral component corresponding to a spectral perturbation, and a third spectral component corresponding to fuel matrix fluorescence.

A forty-eighth aspect, which is the method of the forty-seventh aspect, wherein the step (c) of deriving a signal intensity corresponding to the fuel marker from each measured emission spectrum comprises (1) deconvoluting each measured emission spectrum to yield a deconvoluted measured emission spectrum, wherein deconvoluting each measured emission spectrum comprises the removal of the third spectral component from the measured emission spectrum to yield the deconvoluted measured emission spectrum, and wherein the deconvoluted measured emission spectrum comprises the first spectral component and the second spectral component; (2) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of at least a portion of the second spectral component to yield the corrected emission spectrum; and (3) determining the signal intensity corresponding to the fuel marker from the corrected emission spectrum.

A forty-ninth aspect, which is the method of the forty-seventh aspect, wherein the projection function is fuel marker specific.

A fiftieth aspect, which is the method of any one of the forty-first through the forty-ninth aspects, wherein the fuel sample is a liquid sample.

A fifty-first aspect, which is the method of any one of the forty-fist through the fiftieth aspects, wherein the excitation source comprises a light-emitting diode (LED) and/or a laser diode.

A fifty-second aspect, which is the method of any one of the forty-first through the fifty-first aspects, wherein the fuel comprises gasoline, diesel, jet fuel, kerosene, liquefied petroleum gas, non-petroleum derived fuels, alcohol fuels, ethanol, methanol, propanol, butanol, biodiesel, maritime fuels, or combinations thereof; and wherein the fuel marker is present in the fuel sample in an amount of from about 0.1 ppb to about 1,000 ppb, based on the total weight of the fuel sample.

A fifty-third aspect, which is the method of any one of the forty-first through the fifty-second aspects further comprising determining adulteration of the fuel by comparing the amount of fuel marker in the fuel sample to a target amount of fuel marker, wherein the target amount of fuel marker is a known amount of fuel marker used to mark the fuel by a fuel supplier.

A fifty-fourth aspect, which is the method of any one of the forty-first through the fifty-third aspects, wherein the two or more measured emission spectra of the fuel sample comprise three measured emission spectra of the fuel sample.

A fifty-fifth aspect, which is a method of fuel analysis comprising (a) acquiring a fuel sample; (b) placing the fuel sample in a portable fluorescence spectrometer; wherein the fluorescence spectrometer comprises a temperature-controlled detector and a temperature-controlled excitation source; wherein the temperature-controlled detector and the temperature-controlled excitation source are characterized by a spectrometer temperature; wherein the fuel sample is not temperature-controlled; wherein the fuel sample is characterized by a sample temperature, and wherein the sample temperature is different from the spectrometer temperature; wherein the fuel comprises a fuel marker and a fuel matrix; wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively; (c) acquiring, via the fluorescence spectrometer, three measured emission spectra of the fuel sample during the first half of the equilibration time period; (d) deriving a signal intensity corresponding to the fuel marker from each measured emission spectrum; (e) generating a signal intensity variation over time curve and a sample temperature variation over time curve, wherein the signal intensity decreases with the sample temperature increasing over time or increases with the sample temperature decreasing over time; and wherein the signal intensity decrease or increase follows an exponential decay or growth curve over time, respectively; (f) estimating a signal intensity corresponding to the fuel marker at the end of the equilibration time period; (g) determining the amount of fuel marker in the fuel sample from the estimated signal intensity corresponding to the fuel marker at the end of the equilibration time period; and (h) determining adulteration of the fuel by comparing the amount of fuel marker in the fuel sample to a target amount of fuel marker, wherein the target amount of fuel marker is a known amount of fuel marker used to mark the fuel by a fuel supplier.

A fifty-sixth aspect, which is the method of the fifty-fifth aspect, wherein the step (a) of acquiring a fuel sample further comprises determining the presence of the fuel marker in the fuel sample.

A fifty-seventh aspect, which is a method of spectra correction comprising (a) placing a sample in a spectrometer; wherein the spectrometer comprises a temperature-controlled detector and a temperature-controlled excitation source; wherein the temperature-controlled detector and the temperature-controlled excitation source are characterized by a spectrometer temperature; wherein the sample is not temperature-controlled; wherein the sample is characterized by a sample temperature, and wherein the sample temperature is different from the spectrometer temperature; wherein the sample comprises an analyte; wherein the sample, when allowed to equilibrate to the spectrometer temperature, undergoes a sample temperature increase or decrease to the spectrometer temperature over an equilibration time period; wherein the sample temperature increase or decrease follows an exponential growth or decay curve over time, respectively; (b) acquiring, via the spectrometer, two or more measured spectra of the sample during the first half of the equilibration time period; (c) deriving a signal intensity corresponding to the analyte from each measured spectrum; (d) generating a signal intensity variation over time curve and a sample temperature variation over time curve, wherein the signal intensity decreases with the sample temperature increasing over time or increases with the sample temperature decreasing over time; and wherein the signal intensity decrease or increase follows an exponential decay or growth curve over time, respectively; (e) estimating a signal intensity corresponding to the analyte at the end of the equilibration time period; and (f) determining the amount of analyte in the sample from the estimated signal intensity corresponding to the analyte at the end of the equilibration time period.

A fifty-eighth aspect, which is the method of the fifty-seventh aspect, wherein the spectrometer is portable.

A fifty-ninth aspect, which is the method of any one of the fifty-seventh and the fifty-eighth aspects, wherein the steps (c), (d), and (e) are spectrometer specific.

A sixtieth aspect, which is the method of any one of the fifty-seventh through the fifty-ninth aspects, wherein the two or more measured spectra of the sample comprise three measured spectra of the sample.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of fuel analysis comprising:
   (a) subjecting a fuel sample to fluorescence spectroscopy to generate a measured emission spectrum, wherein the fuel comprises a fuel marker and a fuel matrix, and wherein the measured emission spectrum comprises a first spectral component corresponding to type and amount of fuel marker in the fuel sample, a second spectral component corresponding to a spectral perturbation, and a third spectral component corresponding to fuel matrix fluorescence;
   (b) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component;
   (c) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of at least a portion of the second spectral component to yield the corrected emission spectrum; and
   (d) determining the amount of fuel marker in the fuel sample from the corrected emission spectrum.

2. The method of claim 1, wherein the step (b) of deconvoluting the measured emission spectrum comprises removal of additive fuel matrix fluorescence baseline via a three-step process, wherein the three-step process comprises (i) an iterative fit of the measured emission spectrum to a reference spectrum to yield a residual spectrum; (ii) applying shape-preserving piecewise cubic hermite interpolating polynomial (pchip) to the residual spectrum to yield a reconstituted residual spectrum; and (iii) subtracting the reconstituted residual spectrum from the measured emission spectrum to yield the deconvoluted measured emission spectrum.

3. The method of claim 1, wherein the step (c) of decoupling the deconvoluted measured emission spectrum comprises the removal of multiplicative fuel matrix perturbation via the projection function.

4. The method of claim 1, wherein the spectral perturbation comprises fuel matrix effects that induce spectral inconsistencies in similarly marked fuel samples.

5. The method of claim 1, wherein the spectral perturbation comprises solvatochromism.

6. The method of claim 1, wherein the projection function is derived by comparing an emission fluorescence spectrum of a marked fuel sample comprising a known amount of fuel marker and fuel with an emission fluorescence spectrum of one or more marked solvent solutions comprising a known amount of fuel marker and a solvent.

7. The method of claim 6, wherein comparing an emission fluorescence spectrum of a marked fuel sample with an emission fluorescence spectrum of one or more marked solvent solutions further comprises principal components regression analysis.

8. The method of claim 1, wherein the projection function is derived by comparing an emission fluorescence spectrum of a marked fuel sample comprising a spectral perturbation with an emission fluorescence spectrum of the same marked fuel sample that has been chemically pre-treated to remove at least a portion of the spectral perturbation.

9. The method of claim 8, wherein comparing an emission fluorescence spectrum of a marked fuel sample with an emission fluorescence spectrum of the chemically pre-treated marked fuel sample comprises determining a least square estimator of a multiple linear regression (MLR) model that fits the emission fluorescence spectrum of the marked fuel sample to the emission fluorescence spectrum of the chemically pre-treated marked fuel sample.

10. The method of claim 8, wherein the subspace devoid of the second spectral component is based on the emission fluorescence spectrum of the chemically pre-treated marked fuel sample.

11. The method of claim 8, wherein the subspace devoid of the second spectral component is derived from the emission fluorescence spectrum of the chemically pre-treated marked fuel sample via matrix decomposition analysis using singular value decomposition (SVD) or principal components analysis (PCA).

12. The method of claim 1, wherein the step (d) of determining the amount of fuel marker in the fuel sample comprises a least square fitting of the corrected emission spectrum to an emission fluorescence spectrum of one or more marked solvent solutions comprising a known amount of fuel marker and a solvent.

13. The method of claim 1, wherein the step (d) of determining the amount of fuel marker in the fuel sample comprises partial least squares (PLS) regression.

14. The method of claim 1, wherein the fuel comprises gasoline, diesel, jet fuel, kerosene, liquefied petroleum gas, non-petroleum derived fuels, alcohol fuels, ethanol, methanol, propanol, butanol, biodiesel, maritime fuels, or combinations thereof.

15. The method of claim 1, wherein the fuel marker is present in the fuel sample in an amount of from about 0.1 ppb to about 1,000 ppb, based on the total weight of the fuel sample.

16. The method of claim 1 further comprising determining adulteration of the fuel by comparing the amount of fuel marker in the fuel sample to a target amount of fuel marker, wherein the target amount of fuel marker is a known amount of fuel marker used to mark the fuel by a fuel supplier.

17. A method of fuel analysis comprising:
(a) acquiring a fuel sample;
(b) subjecting the fuel sample to fluorescence spectroscopy to generate a measured emission spectrum, wherein the fuel comprises a fuel marker and a fuel matrix, wherein the measured emission spectrum comprises a first spectral component corresponding to type and amount of fuel marker in the fuel sample, a second spectral component corresponding to a spectral perturbation, and a third spectral component corresponding to fuel matrix fluorescence, and wherein the spectral perturbation comprises fuel marker solvatochromism;
(c) deconvoluting the measured emission spectrum to yield a deconvoluted measured emission spectrum, wherein deconvoluting the measured emission spectrum comprises the removal of the third spectral component from the measured emission spectrum to yield the deconvoluted measured emission spectrum, and wherein the deconvoluted measured emission spectrum comprises the first spectral component and the second spectral component;
(d) decoupling the deconvoluted measured emission spectrum to yield a corrected emission spectrum via a projection function, wherein the corrected emission spectrum comprises the first spectral component, and wherein the projection function orthogonally projects the deconvoluted measured emission spectrum onto a subspace devoid of the second spectral component to yield the corrected emission spectrum;
(e) determining the amount of fuel marker in the fuel sample from the corrected emission spectrum; and
(f) determining adulteration of the fuel by comparing the amount of fuel marker in the fuel sample to a target amount of fuel marker, wherein the target amount of fuel marker is a known amount of fuel marker used to mark the fuel by a fuel supplier.

18. The method of claim 17, wherein the step (a) of acquiring a fuel sample further comprises determining the presence of the fuel marker in the fuel sample.

19. The method of claim 17, wherein the fuel sample is a liquid sample.

20. The method of claim 17, wherein the projection function is fuel marker specific.

* * * * *